(12) United States Patent
Hostetler et al.

(10) Patent No.: US 8,193,167 B2
(45) Date of Patent: *Jun. 5, 2012

(54) PHARMACOLOGICALLY ACTIVE AGENTS CONTAINING ESTERIFIED PHOSPHONATES AND METHODS FOR USE THEREOF

(75) Inventors: Karl Y. Hostetler, Del Mar, CA (US); W. Brad Wan, Oceanside, CA (US)

(73) Assignees: The Regents of the University of California, Oakland, CA (US); The United States of America, Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/635,644

(22) Filed: Dec. 10, 2009

(65) Prior Publication Data

US 2010/0273742 A1  Oct. 28, 2010

Related U.S. Application Data

(63) Continuation of application No. 11/053,198, filed on Feb. 7, 2005, now Pat. No. 7,652,001.

(60) Provisional application No. 60/542,522, filed on Feb. 5, 2004.

(51) Int. Cl.
*A01N 57/00* (2006.01)
*A01N 57/10* (2006.01)
*A61K 31/66* (2006.01)
*C07F 9/02* (2006.01)
*C07D 279/00* (2006.01)
*C07D 285/00* (2006.01)
*C07D 295/00* (2006.01)

(52) U.S. Cl. ........... 514/75; 514/143; 568/8; 544/3
(58) Field of Classification Search .......... 514/75, 514/143; 568/8; 544/3
See application file for complete search history.

(56) References Cited

U.S. PATENT DOCUMENTS

| | | |
|---|---|---|
| 3,404,178 A | 10/1968 | Roy et al. |
| 3,442,021 A | 5/1969 | Lelis |
| 3,468,935 A | 9/1969 | Peck |
| 3,710,795 A | 1/1973 | Higuchi et al. |
| RE28,819 E | 5/1976 | Thompson |
| 4,044,126 A | 8/1977 | Cook et al. |
| 4,327,039 A | 4/1982 | Blum et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,870,063 A | 9/1989 | Binderup et al. |
| 4,927,814 A | 5/1990 | Gall et al. |
| 5,033,252 A | 7/1991 | Carter |
| 5,043,437 A | 8/1991 | Khorlin et al. |
| 5,047,533 A | 9/1991 | Reist et al. |
| 5,052,558 A | 10/1991 | Carter |
| 5,142,051 A | 8/1992 | Holy et al. |
| 5,183,815 A | 2/1993 | Saari et al. |
| 5,196,409 A | 3/1993 | Breuer et al. |
| 5,247,085 A | 9/1993 | Harnden et al. |
| 5,300,671 A | 4/1994 | Tognella et al. |
| 5,300,687 A | 4/1994 | Schwender et al. |
| 5,312,954 A | 5/1994 | Breuer et al. |
| 5,323,907 A | 6/1994 | Kalxelage |
| 5,354,853 A | 10/1994 | Staveski et al. |
| 5,395,826 A | 3/1995 | Naumann et al. |
| 5,411,947 A | 5/1995 | Hostetler et al. |
| 5,428,181 A | 6/1995 | Sugioka et al. |
| 5,441,946 A | 8/1995 | Pauls et al. |
| 5,442,101 A | 8/1995 | Hanhijarvi et al. |
| 5,463,092 A | 10/1995 | Hostetler et al. |
| 5,484,809 A | 1/1996 | Hostetler et al. |
| 5,554,728 A | 9/1996 | Basava et al. |
| 5,563,128 A | 10/1996 | Pauls et al. |
| 5,579,542 A | 12/1996 | Hayman |
| 5,580,571 A | 12/1996 | Hostetler |
| 5,633,159 A | 5/1997 | Pearson et al. |
| 5,654,286 A | 8/1997 | Hostetler |
| 5,656,745 A | 8/1997 | Bischofberger et al. |
| 5,672,697 A | 9/1997 | Buhr et al. |
| 5,696,277 A | 12/1997 | Hostetler et al. |
| 5,709,874 A | 1/1998 | Hanson et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,116 A | 5/1998 | Hostetler |
| 5,760,013 A | 6/1998 | Hwu et al. |
| 5,780,617 A | 7/1998 | van den Bosch et al. |

(Continued)

FOREIGN PATENT DOCUMENTS

EP  0 186 405 B1  12/1985

(Continued)

OTHER PUBLICATIONS

Merck Manual Home Edition, subject "Viral Infections" [online], [Retrieved on Oct. 16, 2008]. Retrieved from the internet <http://www.merck.com/mmhe/print/sec17/ch198/ch198a.html>.*

Aldern, K.A. et al., "Increased antiviral activity of 1-O-hesadecyloxypropyl-12-(14)C}cidofovir in MRC-5 human lung fibroblasts is explained by unique cellular uptake and metabolism." *Mol Pharmacol.* 63(3):678-81 (Mar. 2003).

Balazarini, J. et al., "Antiretroviros Activity of a Novel Class of Acyclic Pyrimdine Nucleoside Phosphonates" *American Society for Microbiology, Antimicrobial Agents and Chemotherapy*, 2185-2193 (Jul. 2002).

Beadle, J.R. et al., "Alkoxyalkyl esters of cidofovir and cyclic cidofovir exhibit multiple-log enhancement of antiviral activity against cytomegalovirus and herpes virus replication in vitro" *Antimicrob Agents Chemother.* 46(8):2381-6 (Aug. 2002).

(Continued)

*Primary Examiner* — Scarlett Goon
(74) *Attorney, Agent, or Firm* — Kilpatrick Townsend & Stockton LLP

(57) ABSTRACT

Compounds and compositions are provided for treatment, prevention, or amelioration of a variety of medical disorders associated with viral infections, cell proliferation and bone metabolism. The compounds provided herein are alkyl esters of phosphonates.

10 Claims, No Drawings

U.S. PATENT DOCUMENTS

| | | | |
|---|---|---|---|
| 5,792,756 | A | 8/1998 | Starrett, Jr. et al. |
| 5,798,340 | A | 8/1998 | Bischofberger et al. |
| 5,804,552 | A | 9/1998 | Basava et al. |
| 5,817,638 | A | 10/1998 | Hostetler |
| 5,827,831 | A | 10/1998 | Hostetler et al. |
| 5,840,674 | A | 11/1998 | Yatvin et al. |
| 5,840,716 | A | 11/1998 | Ubasawa et al. |
| 5,854,228 | A | 12/1998 | Webb, II et al. |
| 5,856,314 | A | 1/1999 | Kaas et al. |
| 5,860,957 | A | 1/1999 | Jacobsen et al. |
| 5,869,468 | A | 2/1999 | Freeman |
| 5,877,166 | A | 3/1999 | Reist et al. |
| 5,879,700 | A | 3/1999 | Hostetler |
| 5,885,973 | A | 3/1999 | Papapoulos et al. |
| 5,886,179 | A | 3/1999 | Arimilli et al. |
| 5,900,252 | A | 5/1999 | Calanchi et al. |
| 5,922,695 | A | 7/1999 | Arimilli et al. |
| 5,922,696 | A | 7/1999 | Casara et al. |
| 5,948,433 | A | 9/1999 | Burton et al. |
| 5,972,366 | A | 10/1999 | Haynes et al. |
| 5,977,089 | A | 11/1999 | Arimilli |
| 5,983,134 | A | 11/1999 | Ostrow |
| 5,985,307 | A | 11/1999 | Hanson et al. |
| 5,985,317 | A | 11/1999 | Venkateshwaran et al. |
| 6,002,029 | A | 12/1999 | Hostetler et al. |
| 6,004,534 | A | 12/1999 | Langer et al. |
| 6,010,715 | A | 1/2000 | Wick et al. |
| 6,015,573 | A | 1/2000 | Hostetler |
| 6,024,975 | A | 2/2000 | D'Angelo et al. |
| 6,039,975 | A | 3/2000 | Shah et al. |
| 6,043,230 | A | 3/2000 | Arimilli et al. |
| 6,048,736 | A | 4/2000 | Kosak |
| 6,057,305 | A | 5/2000 | Holy et al. |
| 6,060,082 | A | 5/2000 | Chen et al. |
| 6,069,249 | A | 5/2000 | Arimilli et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,252,060 | B1 | 6/2001 | Hostetler |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,448,392 | B1 | 9/2002 | Hostetler et al. |
| 6,599,887 | B2 | 7/2003 | Hostetler et al. |
| 6,653,296 | B1 | 11/2003 | Holy et al. |
| 6,686,462 | B2 | 2/2004 | Rosowsky et al. |
| 6,716,825 | B2 | 4/2004 | Hostetler et al. |
| 2001/0033862 | A1 | 10/2001 | Hostetler et al. |
| 2003/0207843 | A1 | 11/2003 | Hostetler et al. |
| 2004/0019232 | A1 | 1/2004 | Hostetler et al. |
| 2004/0127735 | A1 | 7/2004 | Hostetler et al. |
| 2005/0176673 | A1 | 8/2005 | Hostetler et al. |
| 2005/0182019 | A1 | 8/2005 | Hostetler et al. |
| 2005/0192246 | A1 | 9/2005 | Hostetler et al. |

FOREIGN PATENT DOCUMENTS

| | | |
|---|---|---|
| EP | 0 269 947 B1 | 11/1987 |
| EP | 0 481 214 B1 | 4/1992 |
| EP | 0 753 523 A1 | 7/1995 |
| WO | WO 92/07065 | 4/1992 |
| WO | WO 93/15187 | 8/1993 |
| WO | WO 95/18816 | 7/1995 |
| WO | WO 01/39724 A2 | 6/2001 |
| WO | WO 01/78749 A1 | 10/2001 |
| WO | WO 02/08446 A2 | 1/2002 |

OTHER PUBLICATIONS

Beadle, J.R. et al., "Synthesis and antiviral evaluation of alkoxyalkyl derivatives of 9-(S)-(3-hydroxy-2-phosphonomethoxypropyl) adenine against cytomegalovirus and orthopoxviruses" *J Mod Chem.*: 49(6):2010-5 (Mar. 23, 2006).

Bindanset, D.J. et al., "Oral activity ether lipid ester prodrugs ofcidofovir against experimental human cytomegalovirus infection" *J Infect Dis.* 190(3):499-503. Epub Jul. 1, 2004 (Aug. 1, 2004).

Brachwitz, H. et al., "Berdel WE. 1-β-D-Arabinofuranoslcytosine-5'-alkylphosphonophophates and diphosphates: new orally active derivatives of ara-C" *Journal of Lipid Research*. 39:162-172 (1988).

Brachwitz, H. et al., "New nucleoside-5'-alkylphosphonophosphates and related compounds containing 2'-deoxycytidine, thymidine and adenosine as nucleoside component. Syntheses and their effects on tumor cell growth in vitro" *Chemistry and Physics of Lipids* 87:31-39 (1997).

Brachwitz, H. et al., "Synthesis and cytostatical evaluation of cytidine- and adenosine-5'-hexadecylphosphate and their phosphonate analogs" *Chemistry and Physics of Lipids* 90:143-149 (1997).

Bueller, R.M. et al., "Efficacy of oral active ether lipid analogs of cidofovir in a lethal mousepox model" *Virology*. 318(2):474-81 (Jan. 20, 2004).

Cheng, L. et al., "Characterization of a novel intraocular drug-delivery system using crystalline lipid antiviral produgs of ganciclovir and cyclic cidofovir" *Invest Opthalmol Via Sci*. 45(11):4138-44 (Nov. 2004).

Cheng, L. et al., "Ganciclovir release rates in vitreous from different formulations of I-O-hexadecylpropanediol-3-phospho-ganciclovir" *J Ocul Phamacol Ther*. 19(2):161-9 (Apr. 2003).

Cheng, L. et al., "Intravitreal toxicology and duration of efficacy of a novel antiviral lipid prodrug of ganciclovir in liposome formulation" *Invest Ophthalmol Vis Sci*. 41(6):1523-32 (May 2000).

Cheng, L. et al., "Treatment or prevention of herpes simplex virus retinitis with intravitreally injectable crystalline 1-O-hecadecylpropanediol-3-phospho-ganciclovir" *Invest Ophtalmol Vis Sci*. 43(2):515-21 (Feb. 2002).

Ciesla, S.L. et al., "Esterification of cidofovir with alkoxyalkanols increases oral bioavailability and diminishes drug accumulation in kidneys" *Antiviral Res*. 59(3):163-71 (Aug. 2003).

English Abstract of WO 01/78749 A1 (2001).

Hartline, C.B. et al., "Ether lipid-ester prodrugs of acyclic nucleoside phosphonates: activity against adenovirus replication in vitro" *J Infect Dis*. 191(2):396-9 (Feb. 1, 2005).

Hockova, D. et al., "5-Substituted-2,4-diamino-6-(2 (phosponomethoxy)ethoxylpyrimidines-acyclic nucleoside phosphonate analogues with antiviral activity" *J Med Chem*. 46:5064-73 (2003).

Holy, A. et al., "6-[2-(Phosphonomethoxy)alkoxylpyrimidines with Antiviral Activity" *J Med Chem* 45:1918-29 (2002].

Hong, C. et al., "Nucleoside Conjugates 6. synthesis and comparison of Antitumor activity of 1-β-D-Arabinofuranosylcytosine conjugates of Corticosteroids and Selected Lipophilic Alcohols" J Mod Chem 28:171-77 (1985).

Hosteter, K.Y. et al. "Lipid prodrugs of phosphonoacids: greatly enhanced antiviral activity of 1-O-octadocyl-sn-glycero-3-phosphonoformate in HIV-1, HSV-1 and HCMV-infected cells, in vitro." *Antiviral Research*, v. 31:(1996), p. 59-67.

Hostetler, K.Y. et al., "Enhanced antiproliferative effects of alkoxyalkyl esters of cidofovir in human cervical cancer cells in vitro" *Mol Cancer Ther*. 5(1):156-9 (Jan. 2006).

Hostetler, K.Y. et al., In vitro and in vivo activity of 1-O-hexadecylpropanediol-3-phospho-ganciclovir in cytomegalovirus and herpes simplex virus infections. *Antivir Chem Chemother*. 12(1):61.70 (Jan. 2001).

Keith, K.A. et al., "Inhibitory activity of alkoxyalkyl and alkyl esters of cidofovir and cyclic cidofovir against orthopoxvirus replication in vitro" *Antimicrob Agents Chemother*. 48(5):1869-71 (May 2004).

Kern, E.R. et al. "Oral treatment of murine cytomegalovirous infections with ether lipid esters of cidofovir" *Antimicrob Agents Chemother*. 48(9):3516-22 (Sep. 2004).

Kern, E.R. et al., "Efficacy of topical acyclovir monophosphate, acyclovir, or penciclovir in orofacial HSV-1 infections of mice and genital HSV-2 infections of guinea pigs" *Nucleosides Nucleotides Nucleic Acids*. 19(1.2)501-13 (Jan.-Feb. 2000).

Kern, E.R. et al., "Enhanced inhibition of orthopoxvirus replication in vitro by alkoxyalkyl esters of cidofovir and cyclic cidofovir" *Antimicrob Agents Chemother*. 46(4):991.5 (Apr. 2002).

Kini, G.D. et al., "Alkoxy propane prodrugs of foscarnet: effect of alkyl chain length on in vitro antiviral activity in cells infected with HIV-1, HSV-1 and HCMV" *Antiviral Res.* 36(1):43-53 (Sep. 1197).

Lu, S. et al., "Intraocular properties of Hexadecyloxypropyl-Cyclic-Cidofovir in Guinea Pigs" *J Ocul Pharmacol Ther.* 21(3):205-9 (Jun. 2005).

Maloisel, J.-L. et al., "Neoglycolipid conjugates of foscarnet with enhanced antiviral activity in cells infected with human cytomegalovirus and herpes simplex virus type 1." *Antiviral Chemistry & Chemotherapy*, 10(6):333-345 (1999).

McGuigan, C. et al., "Phosphate derivatives of AZT display enhanced selectivity of acting against HIV 1 by comparison to the parent nucleoside" *FEBS Letters*; Fed. of Europ. Bioche. Soc. 310:2:171-74 (1992).

Painter, G.R. et al., "Design and development of oral drugs the prophylaxis and treatment of smallpox infection" *Trends Biotechnol.* 22(8):423-7 (Aug. 2004).

Plotkin, L.I. et al., "Prevention of osteocyte and osteoblast apoptosis bisphosphonates and calcitonin" *J Clin Invest.* 104:1363-74 (Nov. 1999).

Quenelle, D.C. et al., "Oral treatment of cowpox and vaccinia virus infections in mice with ether lipid esters of cidofovir" *Antimicrob Agents Chemother.* 48(2):404-12 (Feb. 2004) *Erratum in: Antimicrob Agents Chemother.* 48(5):1919 (May 2004).

Randhawa, P. et al. "Ether Lipid Ester Derivatives of Cidofovir Inhibit Polyomavirus BK Replication Vitro" *Antimicrob Agents Chemother.* 50(4):1564-6 (Apr. 2006).

Rosowsky, A. et al., Lipophilic 5'-(Alkyl phosphate) Esters of 1-β-D-Arabinofuranosylcytosine and Its $N^4$\{-Acyl and 2,2'-Anhydro-3'-O-acyl Derivatives as Potential Prodrugs. *J Med Chem.* 25:171-78 (1982).

Rosowsky, A. et al., "Synthesis and in vitro activity of long-chain 5'-[(alkoxycarbonyl)phosphinyl]-3'-asido-3'-demythymidines against wild-type and AZT- and foscatnet-resistant strains of HIV-1" *J Med Chem* 40(16):2482-90 (Aug. 1, 1997).

Smee, D.F. et al., "Characterization and treatment of cidofovir-resistant vaccinia (WR strain) virus infections in cell culture and in mice" *Antivir Ch Chemother.* 16(3):203-11 (2005).

Smee, D.F. et al., "Effects of four antiviral substances on lethal vaccine virus (IHD strain) respiratory infections in mice" *Int J Antimicrob Agents.* 23(5):430-7 (May 2004).

Van Beek, E. et al., "Dissociation of Binding and Antiresorptive Properties of Hydroxybisphosphonates by Substitution of the Hydroxyl with an Amino Group" *J Bone and Mini Research* 11(10):1492-97 (1996).

Wan, W.B. et al., Comparison of the antiviral activities of alkoxyalkyl and alkyl esters of cidofovir against human and murine cytomegalovirus replication in vitro. *Antimicrob Agents Chemother.* 49(2):656.62 (Feb. 2005).

Williams-Aziz, S.L. et al., Comparative activities of lipid esters ofcidofovir and cyclic cidofovir against replication of herpesviruses in vitro. *Antimicrob Agents Chemother.* 49(9):3724-33 (Sep. 2005).

* cited by examiner

PHARMACOLOGICALLY ACTIVE AGENTS CONTAINING ESTERIFIED PHOSPHONATES AND METHODS FOR USE THEREOF

RELATED APPLICATION DATA

This application is a continuation of the U.S. application Ser. No. 11/053,198, filed Feb. 7, 2005, which claims priority under 35 U.S.C. §119(e) to U.S. Provisional Application Ser. No. 60/542,522, filed Feb. 5, 2004, entitled "PHARMACOLOGICALLY ACTIVE AGENTS CONTAINING ESTERIFIED PHOSPHONATES AND METHODS FOR USE THEREOF" to Karl Hostetler and Brad Wan, which is are incorporated herein by reference in their entireties.

GRANT INFORMATION

This invention was made with government support under Grant No. EY11832-06 awarded by the National Health Institute/National Eye Institute, and under Grant No. DAMD17-01-2-0071 awarded by the Department of Defense. The United States government has certain rights in this invention.

FIELD

Provided herein are alkyl esters of phosphonate compounds. In one embodiment, the compounds are esterified derivatives of biologically active phosphonates. In another embodiment, provided herein are methods of treatment, prevention, or amelioration of a variety of medical disorders associated with viral infections, cell proliferation and bone metabolism using the compounds and compositions provided herein.

BACKGROUND

Phosphonate compounds have long been known to have antiviral, antiproliferative and other variety of therapeutic benefits. Among these are the antiviral nucleotide phosphonates, such as, for example, cidofovir, cyclic cidofovir, adefovir, tenofovir, and the like, as well as the 5'-phosphonates and methylene phosphonates of azidothymidine (AZT), ganciclovir, acyclovir, and the like. In these compounds, the 5'-hydroxyl of the sugar moiety, or its equivalent in acyclic nucleosides (ganciclovir, penciclovir, acyclovir) which do not contain a complete sugar moiety, is replaced with a phosphorus-carbon bond. In the case of the methylene phosphonates, a methylene group replaces the 5'-hydroxyl or its equivalent, and its carbon atom is, in turn, covalently linked to the phosphonate.

Such compounds may be active as antiviral or antiproliferative nucleotides. Upon cellular metabolism, two additional phosphorylations occur to form the nucleotide phosphonate diphosphate which represents the equivalent of nucleoside triphosphates.

Antiviral nucleotide phosphonate diphosphates are selective inhibitors of viral RNA or DNA polymerases or reverse transcriptases. That is to say, their inhibitory action on viral polymerases is much greater than their degree of inhibition of mammalian cell DNA polymerases $\alpha$, $\beta$ and $\gamma$ or mammalian RNA polymerases. Conversely, the antiproliferative nucleotide phosphonate diphosphates inhibit cancer cell DNA and RNA polymerases and may show much lower selectivity versus normal cellular DNA and RNA polymerases.

Another class of therapeutically beneficial phosphonate compounds are the bisphosphonates, i.e., pyrophosphate analogs wherein the central oxygen atom of the pyrophosphate bond is replaced by carbon. Various substituent groups may be attached to this central carbon atom to produce derivatives of bisphosphonate compounds having various degrees of pharmacological potency.

Bisphosphonates and their substituted derivatives have the intrinsic property of inhibiting bone resorption in vivo. Bisphosphonates also act by inhibiting apoptosis (programmed cell death) in bone-forming cells. Indications for their use therefore include the treatment and prevention of osteoporosis, treatment of Paget's disease, metastatic bone cancers, hyperparathyroidism, rheumatoid arthritis, algodistrophy, sterno-costo-clavicular hyperostosis, Gaucher's disease, Engleman's disease, and certain non-skeletal disorders.

Although bisphosphonates have therapeutically beneficial properties, they suffer from pharmacological disadvantages as orally administered agents. One drawback is low oral availability: as little as 0.7% to 5% of an orally administered dose is absorbed from the gastrointestinal tract. Oral absorption is further reduced when taken with food. Further, it is known that some currently available bisphosphonates, e.g., FOSAMAX® (Merck; alendronate sodium), SKELID® (Sanofi, tiludronate) and ACTONEL® (Procter and Gamble, risedronate) have local toxicity, causing esophageal irritation and ulceration. Other bisphosphonates, like amino-olpadronate, lack anti-resorptive effects (Van Beek, E. et al., J. Bone Miner Res 11(10): 1492-1497 (1996) but inhibit osteocyte apoptosis and are able to stimulate net bone formation (Plotkin, L. et al., J Clin Invest 104(10):1363-1374 (1999) and U.S. Pat. No. 5,885,973). It would therefore, be useful to develop chemically modified bisphosphonate derivatives that maintain or enhance the pharmacological activity of the parent compounds while eliminating or reducing their undesirable side effects.

The threat of an intentional or an unintentional spread of poxvirus infections to a vulnerable population has led to increased efforts to find safe, rapidly deployable treatments against such infections. Although vaccination is now being offered to some healthcare workers and other first responders, there are valid concerns about potential vaccine risks. Previously reported smallpox vaccine-associated adverse reactions, along with the unknown prevalence of risk factors among today's population has prompted the preparation of guidances for clinicians in evaluating and treating patients with smallpox vaccination complications. Following this guidance, the vaccine is not recommended for those with eczema and other exfoliative skin disorders, those with hereditary or acquired immunodeficiencies, or for pregnant women or women who desire to become pregnant 28 days after vaccination. More recently the Centers for Disease Control issued a health advisory recommending as a precautionary measure that persons with known cardiac disease not be vaccinated at this time. Therefore, the use of antiviral therapy in the event of a poxvirus outbreak or in the treatment of vaccination complications against smallpox virus points to the continued need to examine available antiviral therapies, as well as the development of new and more efficient treatment regimens.

There is, therefore, a continuing need for less toxic, more effective pharmaceutical agents to treat a variety of disorders associated with viral infection, cell proliferation and bone metabolism.

SUMMARY

Provided herein are phosphonate and bisphosphonate alkyl esters and compositions thereof for the treatment of various diseases. In one embodiment, compounds and compositions provided herein have antiviral activity. In another embodiment, provided herein are compounds and compositions that are useful in the treatment, prevention, or amelioration of one or more symptoms associated with cell proliferation. In yet another embodiment, the compounds and compositions are for treating diseases associated with bone metabolism in a subject.

Provided herein are chemically modified phosphonate derivatives of pharmacologically active agents, e.g., antiviral and anti-neoplastic pharmaceutical agents that contain phosphonates. These modified derivatives increase the potency of the parent compound while minimizing deleterious side effects when administered to a subject in need thereof.

In certain embodiments, the compounds are lipophilic esters of phosphonates. In certain embodiments, the lipophilic esters exhibit enhanced activity against cells infected with poxviruses and herpes viruses compared to non-esterified phosphonates.

In one embodiment, the compounds for use in the compositions and methods provided herein have formula I:

wherein $P^x$ is a pharmacologically active phosphonate, O is an oxygen atom, and R is a substituted or unsubstituted C8-C24 alkyl, substituted or unsubstituted C8-C24 alkenyl having from 1 to 6 double bonds or substituted or unsubstituted C8-C24 alkynyl having from 1 to 6 triple bonds, wherein substituents when present are selected from one or more halogen, alkyl, —$OR^w$, —$SR^w$, cycloalkyl or epoxide, where $R^w$ is hydrogen or alkyl and where the alkyl, alkenyl, alkynyl groups may be further substituted or unsubstituted.

Also provided are pharmaceutically-acceptable derivatives, including salts, esters, enol ethers, enol esters, solvates, hydrates and prodrugs of the compounds described herein. Further provided are pharmaceutical compositions containing the compounds provided herein and a pharmaceutically acceptable carrier. In one embodiment, the pharmaceutical compositions are formulated for single dosage administration.

Methods of treating, using the compounds and compositions provided herein are provided. Methods of treating, preventing, or ameliorating one or more symptoms of diseases associated with viral infections, cell proliferation and bone metabolism using the compounds and compositions provided herein are provided. In practicing the methods, effective amounts of the compounds or compositions containing therapeutically effective concentrations of the compounds are administered.

Articles of manufacture are provided containing packaging material, a compound or composition provided herein which is useful for treating, preventing, or ameliorating one or more symptoms of diseases or disorders associated with viral infections, cell proliferation or bone metabolism using the compounds and compositions provided herein, and a label that indicates that the compound or composition is useful for treating, preventing, or ameliorating one or more symptoms of diseases or disorders associated with viral infections, cell proliferation or bone metabolism.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

Phosphonate compounds for use herein are biologically active derivatives of phosphonic acid that can be converted into alkyl esters as described herein. In certain embodiments, the phosphonate compounds for use herein are phosphonate-containing nucleotides or nucleosides which can be derivatized to their corresponding phosphonates. In other embodiments, the phosphonate compounds for use herein are bisphosphonates.

Bisphosphonates are synthetic phosphonic acid derivatives characterized by two carbon-phosphorus bonds. There are no known enzymes that can cleave such bonds with the consequence that bisphosphonates are absorbed, stored and excreted from the body unaltered. Their physiochemical effect is similar to that of pyrophosphate in that they bind strongly to the surface of solid-phase calcium phosphate and by doing so inhibit the formation, delay the aggregation and slow down the dissolution of calcium phosphate crystals.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C(OR) where R is hydrogen, alkyl, alkenyl, alkynyl, and cycloalkyl. Pharmaceutically acceptable enol esters include, but are not limited to, derivatives of formula C=C(OC(O)R) where R is hydrogen, alkyl, alkenyl, alkynyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which α-synuclein fibril formation is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Other prodrugs for use herein are described elsewhere herein.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the present invention encompasses any racemic, optically active, polymorphic, or steroisomeric form, or mixtures thereof, of a compound of the invention, which possesses the useful properties described herein, it being well known in the art how to prepare optically active forms and how to determine antiproliferative activity using the standard tests described herein, or using other similar tests which are will known in the art. Examples of methods that can be used to obtain optical isomers of the compounds of the present invention include the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis—a synthetic technique whereby at least one step of the synthesis uses an enzymatic reaction to obtain an enatiomerically pure or enriched synthetic precursor of the desired enantiomer;

v) chemical asymmetric synthesis—a synthetic technique whereby the desired enantiomer is synthesized from an achiral precursor under conditions that produce assymetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the term "alkyl" refers to a monovalent straight or branched chain or cyclic radical. In certain embodiments, the alkyl group contains from one to twenty-four carbon atoms, including methyl, ethyl, n-propyl, isopropyl, n-butyl, isobutyl, tert-butyl, n-hexyl, octadecyl, nonadecyl, eicosyl, 18-methyl-nonadecyl, 19-methyl-eicosyl, and the like. As used herein lower alkyl refers to alkyl groups of 1 to 6 carbon atoms.

As used herein, "substituted alkyl" refers to alkyl groups further bearing one or more substituents, including, but not limited to substituents selected from lower alkyl, hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, azido, nitro, nitrone, amino, amido, —C(O)H, acyl, oxyacyl, carboxyl, carbamate, sulfonyl, sulfonamide, and sulfuryl, which may be protected or unprotected as necessary, as taught in Greene, et al., Protective Groups in Organic Synthesis, John Wiley and Sons, Second Ed. 1991, hereby incorporated by reference.

As used herein, "alkenyl" refers to straight or branched chain hydrocarbon group having one or more carbon-carbon double bonds. In certain embodiments, the alkenyl group contains from 2 up to 24 carbon atoms, and "substituted alkenyl" refers to alkenyl groups further bearing one or more substituents as set forth above.

As used herein, "alkynyl" refers to straight or branched chain hydrocarbon group having one or more carbon-carbon triple bonds. In certain embodiments, the alkynyl group contains from 2 up to 24 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

The term "nucleoside" as used herein, refers to a molecule composed of a heterocyclic base and a carbohydrate. Typically, a nucleoside is composed of a heterocyclic nitrogenous base in N-glycosidic linkage with a sugar. Nucleosides are recognized in the art to include natural bases (standard), and non-natural bases well known in the art. The carbohydrates include the true sugars found in natural nucleosides or a species replacing the ribofuranosyl moiety or acyclic sugars. The heterocyclic nitrogenous bases are generally located at the 1' position of a nucleoside sugar moiety. Nucleosides generally contain a base and sugar group. The nucleosides can be unmodified or modified at the sugar, and/or base moiety, (also referred to interchangeably as nucleoside analogs, modified nucleosides, non-natural nucleosides, non-standard nucleosides; see for example, Eckstein et al., International PCT Publication No. WO 92/07065 and Usman et al., International PCT Publication No. WO 93/15187). In natural nucleosides the heterocyclic base is typically thymine, uracil, cytosine, adenine or guanine. The carbohydrate shall be understood to mean the true sugar found in natural nucleosides or a species replacing the ribofuranosyl moiety or acyclic sugars. In certain embodiments, acyclic sugars contain 3-6 carbon atoms and include, for example, the acyclic sugar moieties present in acyclovir (—CH2-O—CH2 CH2-OH), ganciclovir (—CH2-O—CH(CH2 OH)—CH2-OH), and the like. Natural nucleosides have the β-D-configuration. The term "nucleoside" shall be understood to encompass unnatural configurations and species replacing the true sugar that lack an anomeric carbon. In natural nucleosides the heteocyclic base is attached to the carbohydrate through a carbon-nitrogen bond. The term "nucleoside" shall be understood to encompass species wherein the heterocyclic base and carbohydrate are attached through a carbon-carbon bond (C-nucleosides).

As used herein "subject" is an animal, typically a mammal, including human, such as a patient.

The phrase "effective amount" as used herein means an amount required for prevention, treatment, or amelioration of one or more of the symptoms of diseases or disorders associated including those associated with viral infection, cell proliferation and/or bone metabolism.

Where the number of any given substituent is not specified (e.g., haloalkyl), there may be one or more substituents present. For example, "haloalkyl" may include one or more of the same or different halogens.

As used herein, the term "parenteral" includes subcutaneous, intravenous, intra-arterial, intramuscular or intravitreal injection, or infusion techniques.

The term "topically" encompasses administration rectally and by inhalation spray, as well as the more common routes of the skin and mucous membranes of the mouth and nose and in toothpaste.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

In certain embodiments, provided herein are alkyl ester derivatives of known phosphonate compounds according to the methods provided herein. In certain embodiments, the alkyl ester derivatives of phosphonates provided herein have improved properties, such as improved pharmacologic activity, or increased oral absorption. In certain embodiments, cellular enzymes, but not plasma or digestive tract enzymes, convert the compounds provided herein to a free phosphonates. In certain embodiments, the phosphonate compounds described herein reduce or eliminate the tendency of co-administered food to reduce or abolish phosphonate absorption, resulting in higher plasma levels of phosphonates and better compliance by patients.

In one embodiment, the alkyl ester compounds for use in the compositions and methods provided herein have formula I:

wherein $P^x$ is a pharmacologically active phosphonate, O is an oxygen atom, and R is a substituted or unsubstituted $C_8$-$C_{24}$ alkyl, substituted or unsubstituted $C_8$-$C_{24}$ alkenyl having from 1 to 6 double bonds or substituted or unsubstituted $C_8$-$C_{24}$ alkynyl having from 1 to 6 triple bonds wherein substituents when present are selected from one or more halogen, alkyl, alkenyl, alkynyl, —$OR^w$, —$SR^w$, cycloalkyl or epoxide, where each $R^w$ is independently hydrogen or alkyl and where the alkyl, alkenyl, alkynyl groups may be substituted or unsubstituted.

In one embodiment, the compounds for use in the compositions and methods provided herein have formula I:

wherein $P^x$ is a pharmacologically active phosphonate, O is an oxygen atom, and R is a substituted or unsubstituted $C_8$-$C_{24}$ alkyl or substituted or unsubstituted $C_8$-$C_{24}$ alkenyl having from 1 to 6 double bonds, wherein substituents when present are selected from one or more halogen, alkyl, —OH, —SH, cycloalkyl, or epoxide.

In certain embodiments, the R group in the alkyl, alkenyl and alkynyl groups in the compounds of formula I contain 8, 10, 12, 13, 14, 15, 16, 17, 18, 19, 20, 21, 22, 23 or 24 carbon atoms and can be straight or branched chain moieties. In certain embodiments, the R group is a $C_{16}$-$C_{23}$ straight or branched chain alkyl or $C_{16}$-$C_{23}$ straight or branched chain alkenyl. In other embodiments, R is a $C_{17}$-$C_{19}$ straight or branched chain alkyl or $C_{17}$-$C_{19}$ straight or branched chain alkenyl. In other embodiments, R is $C_{17}$-alkyl, $C_{18}$-alkyl or $C_{19}$ alkyl. In other embodiments, R is $C_{17}$-alkenyl, $C_{18}$-alkenyl or $C_{19}$ alkenyl. In other embodiments, R is $C_{17}$-$C_{22}$ alkyl. In other embodiments, R is $C_{17}$ alkyl, $C_{18}$ alkyl, $C_{19}$ alkyl, $C_{20}$ alkyl, $C_{21}$ alkyl, or $C_{22}$ alkyl.

In certain embodiments, R is substituted with one or more groups selected from lower alkyl and halo. In certain embodiments, R is substituted with one or more methyl groups. In certain embodiments, R is substituted with one or more fluoro groups. In certain embodiments, R is $C_{16}$-$C_{23}$ alkyl and is substituted with one or more methyl or fluoro groups. In certain embodiments, the methyl group or the fluoro group substituent is present on the penultimate carbon of the alkyl, alkenyl, or alkynyl chain. In certain embodiments, the R is 7-methyl-octyl, 8-methyl-nonyl, 9-methyl-decyl, 10-methyl-undecyl, 11-methyl-dodecyl, 12-methyl-tridecyl, 13-methyl-tetradecyl, 14-methyl-pentadecyl, 15-methyl-hexadecyl, 16-methyl-heptadecyl, 17-methyl-octadecyl, 18-methyl-nonadecyl, 19-methyl-eicosyl, 20-methyl-heneicosyl, 21-methyl-docosyl, 22-methyl-tricosyl, 7-fluoro-octyl, 8-fluoro-nonyl, 9-fluoro-decyl, 10-fluoro-undecyl, 11-fluoro-dodecyl, 12-fluoro-tridecyl, 13-fluoro-tetradecyl, 14-fluoro-pentadecyl, 15-fluoro-hexadecyl, 16-fluoro-heptadecyl, 17-fluoro-octadecyl, 18-fluoro-nonadecyl, 19-fluoro-eicosyl, 20-fluoro-heneicosyl, 21-fluoro-docosyl or 22-fluoro-tricosyl.

Various pharmacologically active phosphonates can be used in the compounds of formula I provided herein. In certain embodiments, $P^x$ is represented by formula II

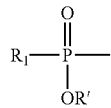

wherein $R_1$ is an antiviral nucleoside or antiproliferative nucleoside, or a bisphosphonate, and R' is selected from an —H, a substituted or unsubstituted straight chain, branched or cyclic C8-C24 alkyl, substituted or unsubstituted C8-C24 alkenyl or C8-C24 alkynyl and wherein substituents when present are selected from one or more halogen, alkyl, alkenyl, alkynyl —OR3, —SR3, cycloalkyl, or epoxide and R3 is a —H or lower alkyl; is —H, or a physiologically acceptable monovalent cation.

Various pharmacologically active phosphonates can be used in the compounds of formula I provided herein. In certain embodiments, $P^x$ is represented by formula II

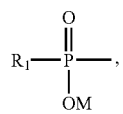

wherein $R_1$ is an antiviral nucleoside or antiproliferative nucleoside, or a bisphosphonate, and M is —H, a physiologically acceptable monovalent cation, a substituted or unsubstituted straight chain, branched or cyclic C8-C24 alkyl, substituted or unsubstituted C8-C24 alkenyl or C8-C24 alkynyl and wherein substituents when present are selected from one or more halogen, alkyl, alkenyl, alkynyl, $OR^w$, —$SR^w$, cycloalkyl or epoxide, where each $R^w$ is independently hydrogen or C1-6 alkyl. In certain embodiments, M is —H, or a physiologically acceptable monovalent cation.

In certain embodiments, $P^x$ is represented by formula II

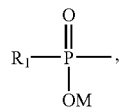

wherein $R_1$ is an antiviral nucleoside or antiproliferative nucleoside, or a bisphosphonate, and M is —H, $Na^+$, $K^+$, or a physiologically acceptable monovalent cation.

In certain embodiments, the compounds provided herein have formula:

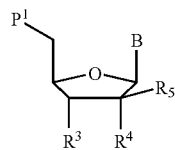

or a pharmaceutically acceptable derivative thereof, wherein $R^3$, $R^4$ and $R^5$ are each H, hydroxy, halo, azido, C1-6 alkyl, C2-6 alkenyl or C2-6 alkynyl; B is a purine or pyrimidine base or analog thereof and $P^1$ is

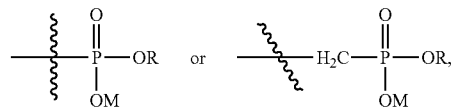

where M and R are as defined elsewhere herein. In certain embodiments, $R^4$ and $R^5$ are selected from hydrogen, halo and hydroxyalkyl. In certain embodiments, $R^4$ and $R^5$ are selected from halo and hydroxyalkyl. In certain embodiments, $R^4$ and $R^5$ are selected from fluoro and hydroxymethyl. In certain embodiments, $R^4$ is selected from fluoro and hydroxymethyl. In certain embodiments, $R^5$ is selected from fluoro and hydroxymethyl.

In certain embodiments, the compounds have formula:

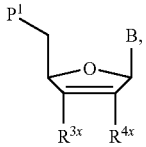

or a pharmaceutically acceptable derivative thereof,
wherein $R^{3x}$ is H, azido, substituted or unsubstituted C1-6 alkyl, substituted or unsubstituted C2-6 alkenyl or substituted or unsubstituted C2-6 alkynyl; $R^{4x}$ is H, C1-6 substituted or unsubstituted alkyl, C2-6 substituted or unsubstituted alkenyl or C2-6 substituted or unsubstituted alkynyl and other variables are as defined elsewhere herein.

In certain embodiments, the compounds have formula:

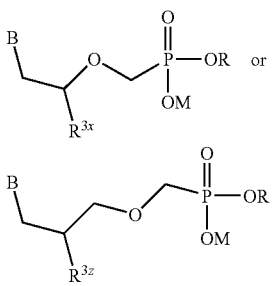

or a pharmaceutically acceptable derivative thereof,
wherein $R^{3z}$ is H, C1-6 alkyl, hydroxyl C1-6 alkyl, halo C1-6 alkyl, azido C1-6 alkyl or OH and the other variables are as defined elsewhere herein. In certain embodiments, $R^{3z}$ is hydrogen C1-6 alkyl or hydroxyl C1-6 alkyl. In certain embodiments, $R^{3z}$ is hydrogen or hydroxy methyl. In certain embodiments, $R^{3z}$ is hydroxy methyl. Optionally, the OH groups are protected, for example as an ester. In certain embodiments, $R^{3z}$ may be in S or R configuration.

In certain embodiments, the compounds have formula:

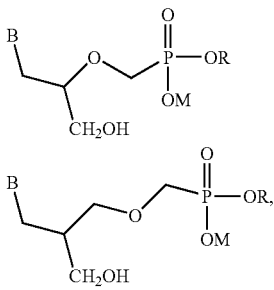

or a pharmaceutically acceptable derivative thereof.
In certain embodiments, the compounds have formula:

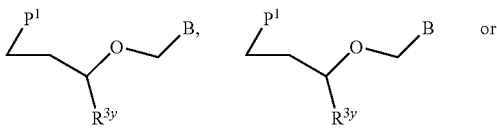

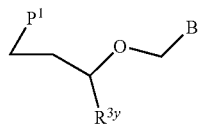

or a pharmaceutically acceptable derivative thereof,
wherein $R^{3y}$ is H, substituted or unsubstituted C1-6 alkyl, substituted or unsubstituted C2-6 alkenyl or substituted or unsubstituted C2-6 alkynyl; or OH and the other variables are as defined elsewhere herein. In certain embodiments, $R^{3y}$ is hydrogen C1-6 alkyl or hydroxyl C1-6 alkyl. In certain embodiments, $R^{3y}$ is hydrogen or hydroxy methyl. In certain embodiments, $R^{3y}$ may be in S or R configuration.

In certain embodiments, B is selected from a natural or non natural purine or pyrimidine base. In certain embodiments, the base is selected from pyrimidin-1-yl, pyrimidin-3-yl, purin-3-yl, purin-7-yl or purin-9-yl residue. In certain embodiments, the base is thymin-1-yl, cytosine-1-yl, adenine-9-yl or guanine-9-yl.

a). $P^x$ as an Antiviral Phosphonate

In certain embodiments, $P^x$ is an antiviral phophonate, including, but not limited to adefovir, cidofovir, cyclic cidofovir, tenofovir, 9-(2-phosphonylmethoxyethyl)guanine (PMEG), 9-(2 phosphonyl-methoxyethyl)adenine (PMEA), penciclovir, and 9-(3hydroxy-2-phosphonylmethoxypropyl) adenine (HPMPA). In certain embodiments, the phosphonates for use in the compounds provided herein contain either a phosphonate (—PO$_3$H$_2$) or a methylene phosphonate (—CH$_2$—PO$_3$H$_2$) group substituted for the 5'-hydroxyl of the antiviral nucleoside. In other embodiments, $P^x$ is a phosphonate derivative of azidothymidine (AZT). In certain embodiments, $P^x$ is cidofovir, cyclic cidofovir, tenofovir or 9-(3hydroxy-2-phosphonylmethoxypropyl)adenine (HPMPA). In certain embodiments, $P^x$ is cidofovir or cyclic cidofovir. In certain embodiments, $P^x$ is 9-(3hydroxy-2-phosphonylmethoxypropyl)adenine.

In certain embodiments, $P^x$ is an antiviral nucleoside, including cyclic and acyclic nucleosides, that can be converted to its corresponding 5'-phosphonate. Such phosphonate analogs typically contain either a phosphonate (—PO$_3$H$_2$) or a methylene phosphonate (—CH$_2$—PO$_3$H$_2$) group substituted for the 5'-hydroxyl of the antiviral nucleoside. Some examples of antiviral phosphonates derived by substituting —PO$_3$H$_2$ for the 5'-hydroxyl are:

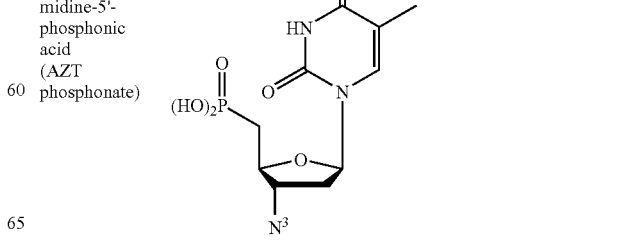

3'-azido-3',5'-dideoxythymidine-5'-phosphonic acid (AZT phosphonate) — Hakimelahi, G. et al.

| | | |
|---|---|---|
| 3',5'-dideoxythymidine2'-ene-5'-phosphonic acid (d4T phosphonate) | 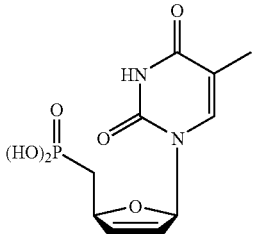 | Hakimelahi, G. et al. |
| 2',3',5'-trideoxycytidine-5'-phosphonic acid (ddC phosphonate) | 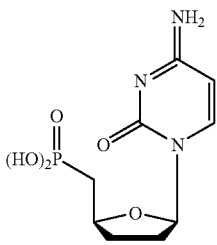 | Kofoed, T., et al. |
| 9-(3-(phosphonomethoxy)propyl)-adenine (Adefovir) | 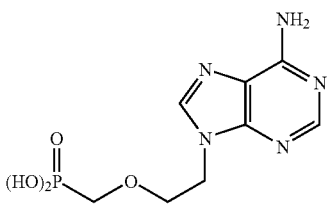 | Kim, et al. |

Some examples of antiviral phosphonates derived by substituting —CH$_2$—PO$_3$H$_2$ for the 5'-hydroxyl are:

| | | |
|---|---|---|
| Ganciclovir phosphonate | 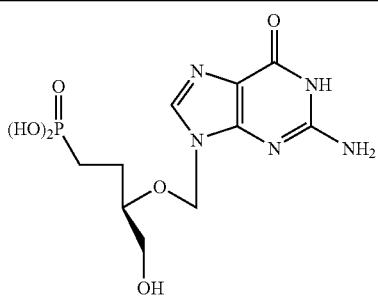 | Huffman, et al. |
| Acyclovir phosphonate | 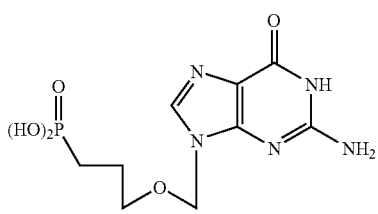 | Huffman, et al. |
| Ganciclovir cyclic phosphonate | 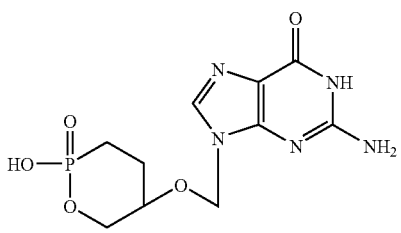 | Smee, et al. |

| | | |
|---|---|---|
| 3'-thia-2',3'-dideoxycytidine-5'-phosphonic acid | 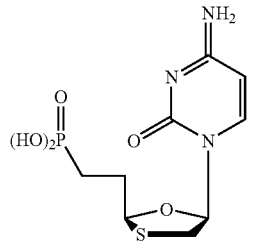 | Kraus, et al. |

In other embodiment, antiviral nucleotide phosphonates for use in the compounds provided herein are obtained from antiviral nucleosides including ddA, ddI, ddG, L-FMAU, DXG, DAPD, L-dA, L-dI, L-(d)T, L-dC, L-dG, FTC, penciclovir, and the like.

b). P$^x$ as an Anti-Neoplastic

In certain embodiment, P$^x$ is an anti-neoplastic selected from a variety of phosphonate-containing nucleotides (or nucleosides which can be derivatized to their corresponding phosphonates).

In other embodiments, P$^x$ is a phosphonate derivative of an anti-neoplastic nucleoside, including, but not limited to cytosine arabinoside, gemcitabine, 5-fluorodeoxyuridine riboside, 5-fluorodeoxyuridine deoxyriboside, 2-chlorodeoxyadenosine, fludarabine, 1-β-D-arabinofuranosyl-guanine, or pharmaceutically acceptable derivatives thereof.

In certain embodiments, P$^x$ is a phosphonate derivative of an anti-neoplastic nucleoside, including, but not limited to 2-chloro-deoxyadenosine, 1-β-D-arabinofuranosyl-cytidine (cytarabine, ara-C), fluorouridine, fluorodeoxyuridine (floxuridine), gemcitabine, cladribine, fludarabine, pentostatin (2'-deoxycoformycin), 6-mercaptopurine, 6-thioguanine, and substituted or unsubstituted 1-β-D-arabinofuranosyl-guanine (ara-G), 1-β-D-arabinofuranosyl-adenosine (ara-A), 1-β-D-arabinofuranosyl-uridine (ara-U).

In certain embodiments P$^x$ is 9-(2-phosphonylmethoxyethyl)guanine (PMEG), 9-(2-(phosponomethoxy)ethyl)-2,6-diaminopurine (PMEDAP), 9-(2-(phosphonomethoxy)ethyl) adenine (adefovir), and the like.

c). P$^x$ as Bisphosphonate

In certain embodiments, P$^x$ is a bisphosphonate, such as for example, alendronate, etidronate, tiludronate, ibandronate, Disodium 1-hydroxy-3-(1-pyrrolidinyl)-propylidene-1,1-bisphosphonate (EB-1053), pamidronate, olpadronate, amino-olpadronate, clodronate, risedronate, and the like.

In certain embodiments, the phosphonates for use in compounds of formula I provided herein are bisphosphonate compounds that have the ability to inhibit squalene synthase and to reduce serum cholesterol levels in a subject. Examples of these bisphosphonates are disclosed, for example, in U.S. Pat. Nos. 5,441,946 and 5,563,128, both of which are hereby incorporated by reference in their entirety. In certain embodiments, the bisphosphonate compounds that have the ability to inhibit squalene synthase are represented by formula:

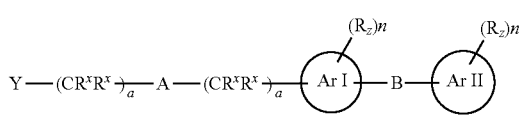

where: A is O, S, NR, SO, SO$_2$ or a bond;
B is (CR$^x$R$^x$)$_{1-2}$, O, S, NR$^x$, SO, SO$_2$, R$^x$C=CR$^x$, C≡C, O=C or a bond;

Y is:

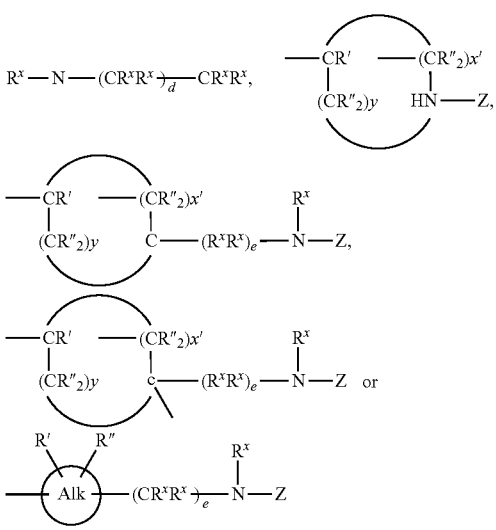

Z is

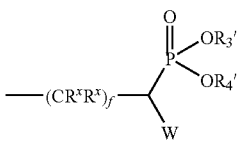

W is H,

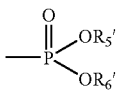

—COOR$_{7'}$ or SO$_3$R$_{8'}$R$_{9'}$; R$^x$ is hydrogen or alkyl;

R' and R" are independently hydrogen, alkyl, alkoxy, hydroxy, halo, haloalkyl or phenyl; or R' and R" together may form a double bond;

each R$^z$ is independently hydrogen, alkyl, alkoxy, hydroxy, halo, haloalkyl or phenyl;

R$_{3'}$, R$_{4'}$, R$_{5'}$, R$_{6'}$, R$_{7'}$, R$_{8'}$, and R$_{9'}$ are independently hydrogen, alkyl, aryl, aralkyl or —CH$_2$OCOR$_x$;

Alk is bi- or tri-carbocycloalkane;

Ar I and Ar II are independently a mono- or di-aryl or heteroaryl;

a and b are independently 0-3;

a+b is 0-4;

d is 0-3;

a+b+d is 1-3;

e is 0-3;

f is 1-6;

m and n are independently 0-2;

x' is 1-6;

y is 0-2;

x'+y is 3-6; and its stereoisomers, enantiomers, diastereoisomers and racemic mixtures; or a pharmaceutically acceptable salt thereof.

d). Other Phosphonates for Use in the Alkyl Ester Compounds of Formula I

Several other phosphonate compounds known to those of skill in the art could be used for preparing the alkyl ester derivatives provided herein. Exemplary phosphonates that can be derivatized as provided are disclosed in the following patents, each of which are hereby incorporated by reference in their entirety: U.S. Pat. No. 3,468,935 (Etidronate), U.S. Pat. No. 4,327,039 (Pamidronate), U.S. Pat. No. 4,705,651 (Alendronate), U.S. Pat. No. 4,870,063 (Bisphosphonic acid derivatives), U.S. Pat. No. 4,927,814 (Diphosphonates), U.S. Pat. No. 5,043,437 (Phosphonates of azidodideoxynucleosides), U.S. Pat. No. 5,047,533 (Acyclic purine phosphonate nucleotide analogs), U.S. Pat. No. 5,142,051 (N-Phosphonylmethoxyalkyl derivatives of pyrimidine and purine bases), U.S. Pat. No. 5,183,815 (Bone acting agents), U.S. Pat. No. 5,196,409 (Bisphosphonates), U.S. Pat. No. 5,247,085 (Antiviral purine compounds), U.S. Pat. No. 5,300,671 (Gem-diphosphonic acids), U.S. Pat. No. 5,300,687 (Trifluoromethylbenzylphosphonates), U.S. Pat. No. 5,312,954 (Bis- and tetrakis-phosphonates), U.S. Pat. No. 5,395,826 (Guanidinealkyl-1,1-bisphosphonic acid derivatives), U.S. Pat. No. 5,428,181 (Bisphosponate derivatives), U.S. Pat. No. 5,442,101 (Methylenebisphosphonic acid derivatives), U.S. Pat. No. 5,532,226 (Trifluommethybenzylphosphonates), U.S. Pat. No. 5,656,745 (Nucleotide analogs), U.S. Pat. No. 5,672,697 (Nuleoside-5'-methylene phosphonates), U.S. Pat. No. 5,717,095 (Nucleotide analogs), U.S. Pat. No. 5,760,013 (Thymidylate analogs), U.S. Pat. No. 5,798,340 (Nucleotide analogs), U.S. Pat. No. 5,840,716 (Phosphonate nucleotide compounds), U.S. Pat. No. 5,856,314 (Thio-substituted, nitrogen-containing, heterocyclic phosphonate compounds), U.S. Pat. No. 5,885,973 (olpadronate), U.S. Pat. No. 5,886,179 (Nucleotide analogs), U.S. Pat. No. 5,877,166 (Enantiomerically pure 2-aminopurine phosphonate nucleotide analogs), U.S. Pat. No. 5,922,695 (Antiviral phosphonomethoxy nucleotide analogs), U.S. Pat. No. 5,922,696 (Ethylenic and allenic phosphonate derivatives of purines), U.S. Pat. No. 5,977,089 (Antiviral phosphonomethoxy nucleotide analogs), U.S. Pat. No. 6,043,230 (Antiviral phosphonomethoxy nucleotide analogs), U.S. Pat. No. 6,069,249 (Antiviral phosphonomethoxy nucleotide analogs); U.S. Pat. Nos. 6,057,305; 6,653,296; Belgium Patent No. 672205 (Clodronate); European Patent No. 753523 (Amino-substituted bisphosphonic acids); European Patent Application 186405 (geminal diphosphonates); and the like. In addition, the compounds listed in the following publications can be derivatized according to the invention to improve their pharmacologic activity, or to increase their oral absorption; each of which are hereby incorporated by reference in their entirety: J. Med. Chem., 2002, 45:1918-1929; J. Med. Chem., 2003, 46:5064-5073; Antimicrob. Agents Chemotherapy, 2002, 46:2185-2193. One of skill in the art would be able to select appropriate phosphonate compounds for use herein.

The following U.S. Patents describe other nucleotide phosphonate analogs: U.S. Pat. No. 5,672,697 (Nucleoside-5'-methylene phosphonates), U.S. Pat. No. 5,922,695 (Antiviral phosphonomethoxy nucleotide analogs), U.S. Pat. No. 5,977,089 (Antiviral phosphonomethoxy nucleotide analogs), U.S. Pat. No. 6,043,230 (Antiviral phosphonomethoxy nucleotide analogs), U.S. Pat. No. 6,069,249, U.S. Pat. No. 5,792,756 (Prodrugs of Phosphonates), U.S. Pat. No. 5,869,468 (Treatment of Conditions of Abnormally Increased Intraocular Pressure by Administration of Phosphonylmethoxyalkyl Nucleoside Analogs and Related Nucleoside Analogs), U.S. Pat. No. 5,854,228 (Antiviral Phosphonomethoxyalkylene Purine and Pyrimidine Derivatives) and U.S. Pat. No. 5,663, 159 (Prodrugs of Phosphonates). Also describing nucleotide phosphonates is EP 0 269 947 (Antiviral phosphonomethoxy-alkylene purine and pyrimidine Derivatives) and EP 0 481 214 (Prodrugs of Phosphonates).

The phosphonates compounds known in the art can be converted in their alkyl ester as described herein. One of skill in the art can easily select an appropriate phosphonate compound for esterification. Some phosphonate compounds that can be esterified are described herein. The appropriate phosphonate for esterification as described herein contains a free —OH group that can be derivatized into its alkyl ester. In certain embodiments, the phosphonate compounds have formula 1:

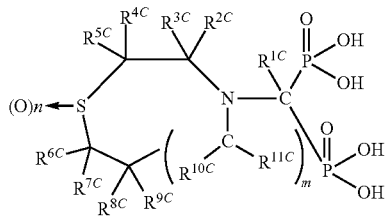

in which $R_{1C}$-$R_{11C}$ can be the same or different and stand for hydrogen, a straight or branched aliphatic or alicyclic $C_1$-$C_{10}$ hydrocarbon radical, an aryl or an aryl-$C_1$-$C_4$-alkyl radical; n is zero or one, and m is zero, one or two, or $R_{2c}$ and $R_{4c}$ when taken together can form a saturated aliphatic 5-, 6- or 7-membered ring which may be substituted with one or more $C_1$-$C_4$-alkyl radicals.

In certain embodiments, the phosphonates for use in the alkyl ester compounds provided herein are represented by formula 2:

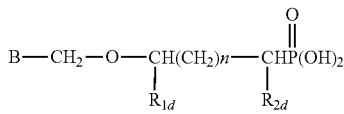

wherein B represents a substituted or unsubstituted purine base, including, but not limited to adenine or guanine and their halogenated derivatives, $R_{1d}$ is selected from H, methyl, hydroxymethyl, halomethyl, azidomethyl, and cyano; $R_{2d}$ is selected from H, methyl, hydroxymethyl, halomethyl, azidomethyl, cyano, and OH; also when $R_{2d}$ is OH, the carbon to which it is attached may be oxidized so that the H there shown and $R_{2d}$ together may be =O; and n is an integer of 0-5.

In other embodiments, the phosphonate compounds for use herein are represented by formula 3:

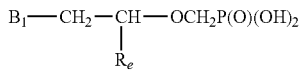

wherein $R_e$ is a hydrogen atom or a hydroxymethyl group and $B_1$ is a pyrimidin-1-yl, pyrimidin-3-yl, purin-3-yl, purin-7-yl or purin-9-yl residue but not an adenin-9-yl residue, and the salts thereof with alkali metals, ammonia or amines.

In other embodiments, the phosphonate compounds for use herein are represented by formula 4:

A2-B2-C2 wherein:

A2 is a residue of a hydroxyl containing steroidal hormone possessing human bone resorption antagonist activity or bone formation stimulatory activity;

C2 is a residue of an amino or hydroxy alkyl-1,1-bisphosphonate, possessing human bone affinity; and B2 is a covalent linkage, connecting A2 through the hydroxyl moiety and C2 through the respective amino or hydroxyl moiety, which linkage can hydrolyze in the human body in the vicinity of bone to release steroidal hormone A2, and pharmaceutically acceptable salts or esters thereof.

In other embodiments, the phosphonate compounds for use herein are represented by formula 5:

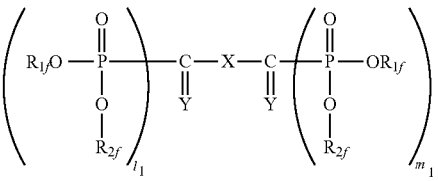

wherein $m_1$ and $l_1$ are independently 1 or 2;

$R_{1f}$ represents hydrogen, a lower alkyl group, or an alkali metal cation;

$R_{2f}$ represents hydrogen, a lower alkyl group or an alkali metal cation;

Y represents =O or =N—OH, or —OH; and

X represents —$(CH_2)n_f$-, a branched alkylene group, or a branched or straight alkenylene or alkynylene chain optionally substituted by one or more oxygen or nitrogen atoms, wherein $n_f$ is an integer from 3 to 24; with the provision that when $l_1$=$m_1$=1, Y is =O, and $R_{1f}$ and $R_{2f}$ denote a lower alkyl group, $n_f$ represents an integer from 9 to 20; and with the provision that when $l_1$=$m_1$=2, Y is —OH and $R_{1f}$ and $R_{2f}$ are methyl groups, $n_f$ represents an integer from 9-24; and with the further provision that when $l_1$=$m_1$=2, Y is —OH and $R_{1f}$ and $R_{2f}$ are hydrogen, $n_f$ represents 3, 5 or an integer from 7 to 24; or X is —$(CH_2)_p$—$(OCH_2CH_2)_q$—O—$(CH_2)p'$-, wherein p and p' are independently integers from 1 to 5 and q is an integer from 1 to 6; or X is —$(CH_2)t$-O—$(CH_2)s$-O—$(CH_2)t'$- wherein t and t' are independently integers from 1 to 6 and s is an integer from 2 to 12; or X is

—B-A-B

Wherein B represents a branched group or straight alkylene, or an alkenylene or alkynylene chain optionally substituted by one or more oxygen or nitrogen atoms, and A represents an aromatic group such as phenylene, naphthalenediyl, thiophenediyl or furandiyl. In certain embodiments, Y represents =O or =N—OH.

In other embodiments, the phosphonate compounds for use herein are represented by formula 6:

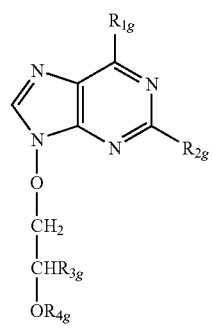

or a pharmaceutically acceptable salt thereof:

wherein $R_{1g}$ is hydroxy, amino, chloro or $OR_{7g}$ wherein $R_{7g}$ is C1-6 alkyl, phenyl or phenyl C1-2 alkyl either of which phenyl moieties may be substituted by one or two substituents selected from halo, C1-4 alkyl or C1-4 alkoxy;

$R_{2g}$ is amino or, when $R_{1g}$ is hydroxy or amino, $R_{2g}$ may also be hydrogen;

$R_{3g}$ is hydrogen, hydroxymethyl or acyloxymethyl;
$R_{4g}$ is a group of formula:

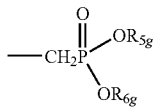

wherein
$R_{5g}$ and $R_{6g}$ are independently selected from hydrogen, C1-6 alkyl and optionally substituted phenyl; or $R_{3g}$ and $R_{4g}$ together are:

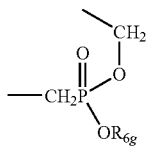

wherein $R_{6g}$ is as defined above.

In other embodiments, the phosphonate compounds for use herein are represented by formula 7:

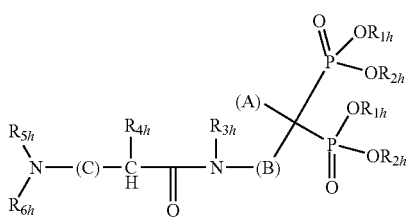

wherein: $R_{1h}$ and $R_{2h}$, which can be the same or different, are hydrogen or C1-C4 alkyl;

(A) is hydrogen, halogen, hydroxy, straight or branched C1-C12 alkyl;

(B) is a covalent bond, a straight or branched C1-C8 alkylene or, together with the adjacent nitrogen atom, a group of formula

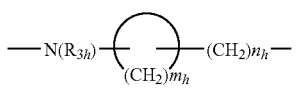

therein the groups —N($R_{3h}$)— and —(CH$_2$)$n_h$- may be in the 1,1; 1,2; 1,3 or 1,4 position of the ring; an ortho, meta or para-substituted aralkylene of formula

an alkylene chain containing at least one hetero-atom of formula —[CH(CH3)]p—(CH2)n1-X—(CH2)$n_h$-; $m_h$ is the integer 5 or 6; $n_h$ and n1 are an integer from 1 to 5; p is zero or 1 and X is O, S, —N—CH$_3$ or the ureido group —NH—CO—NH—; $R_{3h}$ is hydrogen, straight or branched C1-C9 alkyl, C3-C6 cycloalkyl, benzyl, phenyl or p-methoxybenzyl;

(C) is straight or branched C1-C5 alkyl, phenylene, an aralkylene chain of formula

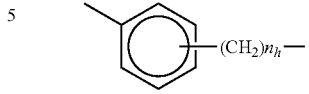

in which $n_h$ is as above defined; $R_{4h}$ is hydrogen, straight or branched C1-C4 alkyl, or it is a group of formula

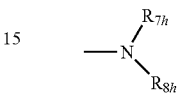

in which $R_{7h}$ and $R_{8h}$, which are the same or different, are hydrogen, straight or branched C1-C6 alkyl, phenyl, benzyl, p-methoxybenzyl, or one of $R_{7h}$ and $R_{8h}$ is as above defined and the other one is a group of formula $R_{9h}$—C(O)—, in which $R_{9h}$ is hydrogen, straight or branched C1-C4 alkyl, phenyl, benzyl, p-methoxyphenyl, straight or branched C1-C4 alkoxy, halo-C1-C4-alkoxy;

$R_{5h}$ and $R_{6h}$ are haloethyl (2-chloroethyl, 2-bromoethyl, 2-iodoethyl) or $R_{5h}$ and $R_{6h}$, together with the nitrogen atom to which they are bound, are a 1-aziridinyl residue of formula

In other embodiments, the phosphonate compounds for use herein are represented by formula 8:

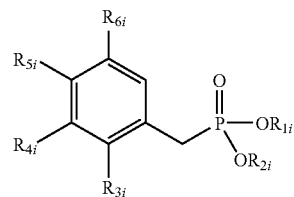

wherein $R_{1i}$ and $R_{2i}$ are the same or different and are selected from any of hydrogen, C1-C8 alkyl, C1-C8 alkenyl, hydroxyalkyl wherein the alkyl portion is C1-C8, alkoxyalkyl wherein the alkyl portion is C1-C8, aralkyl wherein the alkyl portion is C1-C8, such as benzyl, phenylethyl, phenylpropyl, aryl such as phenyl or aminoalkyl, the aminoalkyl includes substituents of the formula —(CH$_2$)n-NR$_{7i}$R$_{8i}$, wherein n=2-6 and $R_{7i}$ and $R_{8i}$ are the same or different and are selected from any of H, C1-C4 alkyl, aralkyl wherein the alkyl portion in C1-C4 or $R_{7i}$ and $R_{8i}$ may be taken together to form a heterocyclic ring having from 5 to 7 ring atoms containing one or more heteroatoms such as N, O and S, examples of suitable ring systems include piperidino, morpholino, tetrahydroquinolinyl, tetrahydroisoquinolinyl, thiomorpholino and piperazino substituted at the N-4 position by $R_{9i}$, wherein $R_{9i}$ is selected from any one of C1-C4 alkyl, or aralkyl wherein the alkyl portion is C1-C4 alkyl or phenyl;

$R_{3i}$ and $R_{5i}$ may each be either H or CF$_3$, with the proviso that only one of $R_{3i}$ or $R_{5i}$ may be CF$_3$ at the same time;

$R_{4i}$ and $R_{6i}$ may each be H or $CF_3$, with the proviso that if either or both of $R_{4i}$ and $R_{6i}$ are CF3, neither $R_{3i}$ nor $R_{5i}$ may be $CF_3$ and with the further proviso that $R_{3i}$-$R_{6i}$ may not each be H at the same time.

In other embodiments, the phosphonate compounds for use herein are represented by tautomeric formula 9a, 9b or 9c

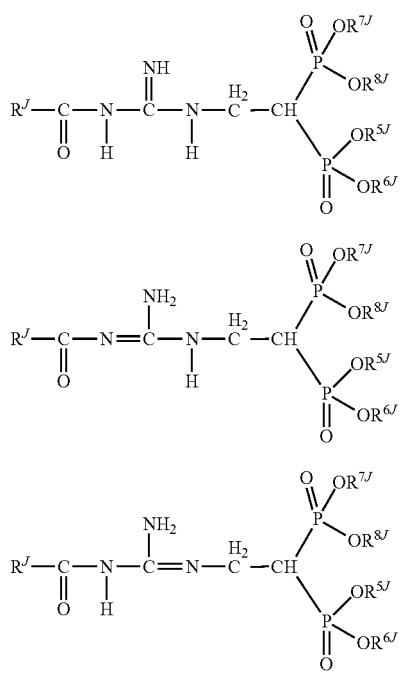

and/or a pharmaceutically acceptable salt of the compound of the formula 9a, 9b or 9c;

$R^J$ has the following meaning therein:

I) a radical of the formula

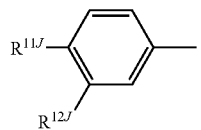

wherein $R^{11J}$ or $R^{12J}$ has the following meaning: a) $R^{13J}$—$S(O)n_{j}$, or b)

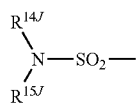

where $R^{13J}$ is 1) (C1-C6)-alkyl, 2) (C5-C7)-cycloalkyl, 3) cyclopentylmethyl, 4) cyclohexylmethyl, 5) phenyl, 6) phenyl substituted once to three times by fluorine atom, chlorine atom, methyl or methoxy, where $n_3$ is the integer zero, 1 or 2, where $R^{14J}$ and $R^{15J}$ are identical or different and have, independently of one another, the following meaning: 1) hydrogen atom, 2) (C1-C6)-alkyl, 3) phenyl, 4) phenyl substituted once or twice by fluorine atom, chlorine atom, methyl or methoxy, 5) —(CH2)$m_j$-phenyl where $m_j$ is an integer from 1 to 4, or 6) —(CH2)$m_j$-phenyl where m is an integer from 1 to 4 and the phenyl radical is substituted once or twice by the radicals indicated in 4, 7) $R^{14J}$ and $R^{15J}$ together form a straight-chain or branched chain of 4 to 7 carbon atoms, the chain can additionally be interrupted by O, S or NR where R is hydrogen or methyl, or 8) $R^{14J}$ and $R^{15J}$ form together with the nitrogen atom to which they bonded a dihydroindole, tetrahydroquinoline or tetrahydroisoquinoline ring, and the other substituent $R^{11J}$ or $R^{12J}$ in each case means a) hydrogen atom, b) halogen atom, such as fluorine, chlorine, bromine or iodine atom, c) (C1-C4)-alkyl, d) (C1-C4)-alkoxy, e) phenoxy, f) phenoxy substituted once to three times by fluorine, chlorine, methyl or methoxy, g) $R^{13J}$—$S(O)n_j$, where $n_j$ is the integer zero, 1 or 2 and $R^{13J}$ has the abovementioned meaning, or h)

where $R^{14J}$ and $R^{15J}$ have the abovementioned meaning, or

II) a radical of the formula

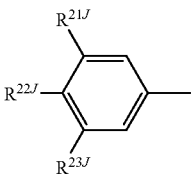

wherein $R^{21J}$, $R^{22J}$ or $R^{23J}$ has the following meaning: a) hydrogen atom, b) halogen atom, such as fluorine, chlorine, bromine or iodine atom, or c) (C1-C12)-alkyl, where one of the substituents $R^{21J}$, $R^{22J}$ or $R^{23J}$ can also mean 1) $N_3$, 2) CN, 3) OH, 4) (C1-C10)-alkoxy, 5) $R^{24J}$—$C_{n_j}H_{2n_j}$—$O_{m_j}$, where $m_j$ is the number zero or 1, nj is the number zero, 1, 2 or 3, $R^{24J}$ is 1) $C_pF_{2p}+1$ where p is the number 1, 2 or 3, as long as $n_j$ is the number zero or 1, 2) (C3-C12)-cycloalkyl, 3) phenyl, 4) pyridyl, 5) quinolyl or 6) isoquinolyl, where the ring system in the radicals 3) to 6) is unsubstituted or substituted by a radical from the group fluorine atom, chlorine atom, CF3, methyl, methoxy or $NR^{25J}R^{26J}$ where $R^{2n}$ and $R^{26J}$ are identical or different and have, independently of one another, the meaning hydrogen atom or (C1-C.4)-alkyl, or III) a radical of the formula

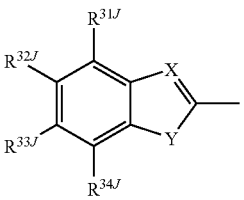

wherein $R^{31J}$, $R^{32J}$, $R^{33J}$ or $R^{34J}$ independently has the following meaning: a) hydrogen atom, b) halogen atom, such as fluorine, chlorine, bromine or iodine atom, or c) —CN, d) —NO2, e) —$N_3$, f)-(C1-C6)-alkyl, straight-chain or branched or g) $R^{35J}$-Cn $H_{2n}$—Z—, where n is the number zero, 1, 2, 3, 4, 5 or 6, and the alkylene chain -Cn H2n- is straight-chain or branched, and one carbon atom can be replaced by an oxygen, sulfur or nitrogen atom, $R^{35J}$ is 1) hydrogen atom, 2) (C3-C6)-alkenyl, 3) (C5-C8)-cycloalkyl, 4) (C5-C8)-cycloalkyl, substituted by a hydroxyl group, or one methylene group is replaced by an oxygen, sulfur or nitrogen atom, or 5) phenyl, unsubstituted or substituted by 1 to 3 radicals from the group halogen atom such as fluorine, chlorine, bromine or iodine atom, $CF_3$; $CH_3$—S(O)x, where x is the number zero, 1 or 2; $R^{36J}$-Wy where $R^{36J}$ is hydrogen atom, methyl or ethyl, W is oxygen atom, NH or $NCH_3$, and y is zero or 1; $C_mF_{2m+1}$, where m is the number 1, 2 or 3; pyridyl; quinolyl or isoquinolyl, Y is $CH_2$ or NH;

Z is

1) —CO—, 2) —$CH_2$—, 3) —[CH(OH))q-, where q is the number 1, 2 or 3, 4) —[$C(CH_3)(OH)$]q-, where q is the number 1, 2 or 3, 5) —O—, 6) —NH—, 7) —$N(CH_3)$—, 8) —S(O)x-, where x is zero, 1 or 2, 9) —$SO_2$-NH— or 10)

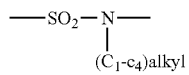

X has the following meaning a) N or b) C—$R^{37J}$, where $R^{37J}$ is hydrogen atom, (C1-C4)-alkyl or (C2-C4)-alkenyl, Y has the following meaning a) NH, b) —N—(C2-C6)-alkyl, c) —N—(C2-C4)-alkenyl or d) $R^{35J}$-Cn H2n-Z—, where $R^{35J}$, n and Z are defined as above, $R^{5J}$, $R^{6J}$, $R^{7J}$ and $R^{8J}$, are identical or different and have, independently of one another, the following meaning a) hydrogen atom, b) (C1-05)-alkyl, straight-chain or branched, or c) phenyl.

In other embodiments, the phosphonate compounds for use herein are represented by formula 10:

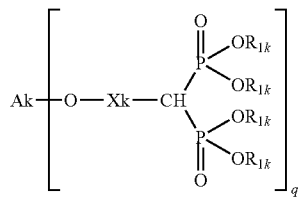

wherein Ak-O— denotes a residue of a compound having an estrogenic activity, $R_{1k}$ independently denotes H or a C1-C6 alkyl group; Xk denotes a single bond, a C1-C10 alkylene group or a group of the formula:

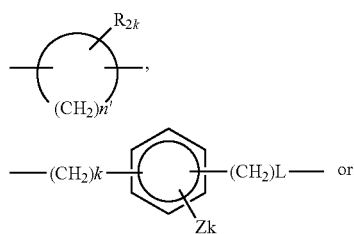

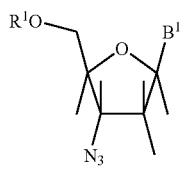

wherein $R_{2k}$ denotes H or a C1-C5 alkyl group; Zk denotes a nitro group or a halogen; n' is an integer of 3 to 12; k is an integer of 1 to 5; L is an integer of 0 to 5; and q is an integer of 1 to 3, and physiologically acceptable salts thereof.

In other embodiments, the phosphonate compounds for use herein are 5'-phosphonates of 3'-azido-2',3'-dideoxynucleosides that are represented by formula 11:

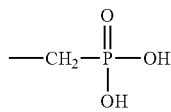

where $R^1$ is

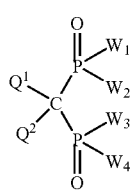

and $B^1$ is thymin-1-yl, cytosine-1-yl, adenine-9-yl or guanine-9-yl.

In other embodiments, the phosphonate compounds for use herein are methylenebisphosphonic acid derivatives represented by formula 10:

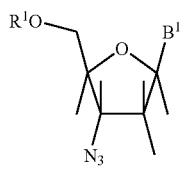

in which $W_1$, $W_2$, $W_3$ and $W_4$ are independently the group $OR_{1m}$ or the group $NR_{2m}R_{3m}$ wherein $R_{1m}$, $R_{2m}$, and $R_{3m}$ independently are hydrogen or straight or branched, optionally unsaturated C1-C22-alkyl, optionally substituted, optionally unsaturated C3-C10-cycloalkyl, aryl, aralkyl or silyl $SiR_{3m}$, or the groups $R_{2m}$ and $R_{3m}$ form together with the adjacent nitrogen atom a 3 to 10-membered saturated, partly saturated or aromatic heterocyclic ring, wherein in addition to the nitrogen atom, there may be one or two heteroatoms from the group N, O and S, provided that in the formula I at least one of the groups $W_1$, $W_2$, $W_3$ and $W_4$ is hydroxy and at least one of the groups $W_1$, $W_2$, $W_3$ and $W_4$ is the amino group $NR_{2m}R_{3m}$, $R_3$, is lower alkyl $Q^1$ and $Q^2$ are independently hydrogen, fluorine, chlorine, bromine or iodine, including the stereoisomers, such as the geometrical isomers and the optically active isomers, of the compounds, as well as the pharmacologically acceptable salts of the compounds.

In other embodiments, the phosphonate compounds for use herein are represented by formula 11:

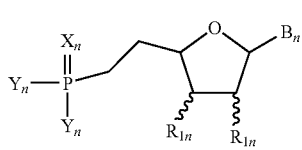

wherein $B_n$ is independently a purine or pyrimidine base or modified form, each $R_{1n}$ is independently hydrogen, hydroxyl, fluorine or methyl ester, each $Y_n$ is independently $OR_{2n}$, $N(R_{2n})_2$ or $SR_{2n}$ wherein, each $R_{2n}$ is independently hydrogen or alkyl (1-12 C); X is selected from oxygen and sulfur.

In other embodiments, the phosphonate compounds for use herein are represented by formula 12:

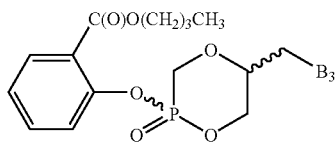

where $B_3$ is a protected or unprotected cytosin-1-yl.

In other embodiments, the phosphonate compounds for use herein are represented by formula 13:

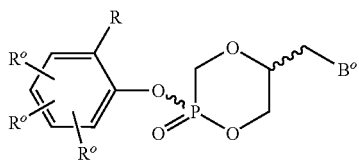

where $B^o$ is a protected or unprotected heterocyclic base;

R is hydrogen (H), alkyl, O-alkyl, —CHO, —C(O)OR$^{2o}$, —C(O)R$^{2o}$, —C(O)N(R$^{3o}$)$_2$ or —S(O)$_2$N(R$^{3o}$)$_2$;

each R$^o$ is independently hydrogen, cyano (CN), nitro (NO$_2$), halogen, alkyl, O-alkyl, —C(O)OR$^{3o}$, —C(O)R$^{3o}$, —S(O)$_2$OH, —N(R$^{3o}$)$_2$, —CHO or —OH; and each R$^{2o}$ and each R$^{3o}$ are independently hydrogen, alkyl, phenyl, alkyl substituted phenyl, —CH$_2$C$_6$H$_5$ or —CH$_2$CH$_2$C$_6$H$_5$.

In other embodiments, the phosphonate compounds for use herein are represented by formula 14:

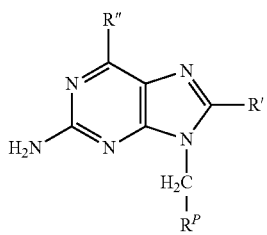

wherein: R$^p$ is selected from the group consisting of

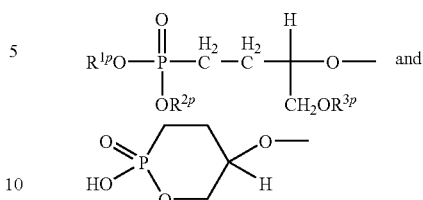

in which R$^{1p}$ and R$^{2p}$ are independently selected from the group consisting of hydrogen and lower alkyl, R$^{3p}$ is lower alkyl or —(CH$_2$)n$_p$—C$_6$H$_5$, and n$_p$ is an integer in the range of 0 to 6 inclusive;

R' is selected from the group consisting of hydrogen, hydroxyl, carboxyl, alkoxy, amino and halogen; and R" is hydrogen or a halogen substituent, or a pharmaceutically acceptable salt or ester thereof.

In other embodiments, the phosphonate compounds for use herein are represented by formula 15:

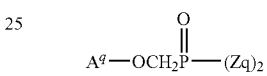

wherein Zq is independently —OC(R$^{2q}$)$_2$OC(O)Xq(R$^q$)$_a$, an ester, an amidate or —H but at least one Zq is —OC(R$^{2q}$)$_2$OC(O)Xq(R$^q$)$_a$;

A$^q$ is the residue of an antiviral phosphonomethoxy nucleotide analog;

Xq is N or O;

R$^{2q}$ independently is —H, C1-C12 alkyl, C5-C12 aryl, C2-C12 alkenyl, C2-C12 alkynyl, C7-C12 alkenylaryl, C7-C12 alkynylaryl, or C6-C12 alkaryl, any one of which is unsubstituted or is substituted with 1 or 2 halo, cyano, azido, nitro or —OR$^{3q}$ in which R$^{3q}$ is C1-C, 12 alkyl, C2-C12 alkenyl, C2-C1 alkynyl or C5-C12 aryl;

R$^q$ independently is —H, C1-C12 alkyl, C5-C12 aryl, C2-C12 alkenyl, C2-C1 alkynyl, C7-C12 alkyenylaryl, C7-C12 alkynylaryl, or C6-C12 alkaryl, any one of which is unsubstituted or is substituted with 1 or 2 halo, cyano, azido, nitro, —N(R$^{4q}$)$_2$ or —OR$^{3q}$, where R$^{4q}$ independently is —H or C1-C8 alkyl, provided that at least one R is not H; and a is 1 when Xq is O, or 1 or 2 when Xq is N;

with the proviso that when a is 2 and Xq is N, (a) two N-linked R$^q$ groups can be taken together to form a carbocycle or oxygen-containing heterocycle, (b) one N-linked R$^q$ additionally can be —OR$^{3q}$ or (c) both N-linked R$^q$ groups can be —H; and the salts, hydrates, tautomers and solvates thereof.

e). Exemplary Esterified Phosphonate Compounds

In certain embodiments, the compounds herein are alkyl esters of cidofovir, cyclic cidofovir or HPMPA. In certain embodiments, the alkyl esters of CDV possess 16-22 carbon atoms. In certain embodiments, the alkyl esters of CDV possess 16, 17, 18, 19, 20, 21 or 22 carbon atoms. In certain embodiments, the alkyl esters of CDV possess 18, 19 or 20 carbon atoms In certain embodiments, the alkyl esters of cidofovir are selected from octyl cidofovir, dodecyl cidofovir, hexadecyl cidofovir, eicosyl cidofovir, docosyl cidofovir and tetracosyl cidofovir. In other embodiment, the alkyl esters of cidofovir are selected from eicosyl cidofovir, docosyl cidofovir and tetracosyl cidofovir. In certain embodiments, the alkyl esters of cidofovir are selected from octyl cyclic cidofovir, dodecyl cyclic cidofovir, hexadecyl cyclic cidofovir, eicosyl cyclic cidofovir, docosyl cyclic cidofovir and cyclic tetracosyl cidofovir. In other embodiment, the alkyl esters of cidofovir are selected from cyclic eicosyl cidofovir, docosyl cyclic cidofovir and tetracosyl cyclic cidofovir. In other embodiment, the alkyl esters of HPMPA is eicosyl-(S)-HPMPA. In certain embodiments, the compounds provided herein are 7-methyl-octyl, 8-methyl-nonyl, 9-methyl-decyl, 10-methyl-undecyl, 11-methyl-dodecyl, 12-methyl-tridecyl, 13-methyl-tetradecyl, 14-methyl-pentadecyl, 15-methyl-hexadecyl, 16-methyl-heptadecyl, 17-methyl-octadecyl, 18-methyl-nonadecyl, 19-methyl-eicosyl, 20-methyl-heneicosyl, 21-methyl-docosyl, 22-methyl-tricosyl, 7-fluoro-octyl, 8-fluoro-nonyl, 9-fluoro-decyl, 10-fluoro-undecyl, 11-fluoro-dodecyl, 12-fluoro-tridecyl, 13-fluoro-tetradecyl, 14-fluoro-pentadecyl, 15-fluoro-hexadecyl, 16-fluoro-heptadecyl, 17-fluoro-octadecyl, 18-fluoro-nonadecyl, 19-fluoro-eicosyl, 20-fluoro-heneicosyl, 21-fluoro-docosyl or 22-fluoro-tricosyl ester of cidofovir or cyclic cidofovir.

In one embodiment, a derivative of cyclic cidofovir is provided which includes an alkyl ester, wherein the alkyl is a C18-22 straight, branched, or cyclic alkyl or alkenyl having 1 to 6 double bonds.

In certain embodiments, the compounds provided herein possess one or more chiral centers, e.g. in the sugar moieties, and may thus exist in optically active forms. Likewise, when the compounds contain an alkenyl group or an unsaturated alkyl or acyl moiety there exists the possibility of cis- and trans-isomeric forms of the compounds. Additional asymmetric carbon atoms can be present in a substituent group such as an alkyl group. The R- and S-isomers and mixtures thereof, including racemic mixtures as well as mixtures of cis- and trans-isomers are contemplated herein. All such isomers as well as mixtures thereof are intended to be included within the scope of the compounds provided herein. If a particular stereoisomer is desired, it can be prepared by methods well known in the art by using stereospecific reactions with starting materials that contain the asymmetric centers and are already resolved or, alternatively, by methods that lead to mixtures of the stereoisomers and resolution by known methods.

C. Preparation of the Compounds

The alkyl ester derivatives of phosphonates for use in the compositions and methods provided herein can be prepared by alkyl esterification of various phosphonate compounds. Exemplary methods for esterification are described herein but other esterification methods well known in the art can be used to prepare the phosphonate alkyl esters provided herein.

Scheme 1 demonstrates a general procedure for esterification of a phosphonate compound by reacting it with a suitable bromoalkane.

Scheme 1

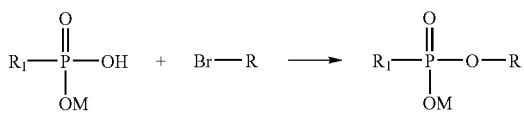

An appropriate 1-bromoalkane (1.2 eq) is added to a suspension of a phosphonate compound in a suitable solvent such as N,N-dicyclohexyl-4-morpholino-carboxamidine (1.1 eq) and N,N-dimethylformamide (10 ml/mmol). The mixture is heated and stirred magnetically overnight. The solvent is then evaporated under reduced pressure, and the residue is purified. The purification can be carried out by methods known to those of skill in the art, including, but not limited to flash column chromatography to isolate the phosphonate alkyl esters.

Scheme 2 demonstrates an alternate general procedure for esterification of a phosphonate compound using Mitsunobu reaction.

Scheme 2

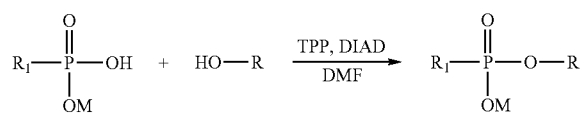

A phosphonate compound (1 eq), an appropriate alkanol (2 eq) and triphenyl phosphine (2 eq) are mixed in anhydrous DMF. The mixture is stirred under nitrogen. Diisopropyl azadicarboxylate (2 eq) is then added in three portions over 15 min before the mixture is allowed to stir overnight. The solvent is then evaporated under vacuum, and the residue is purified by methods known in the art.

The alkyl esters of cyclic cidofovir analogs provided herein can be converted to their corresponding acyclic analogs by procedures known in the art. For example, an alkyl-cCDV analog is suspended in 2 M NaOH (25 ml/mmol). The suspension is heated to 80° C. and stirred for 1 h. After hydrolysis, the solution is cooled to 25° C. and acidified with glacial acetic acid (pH approximately 5). The resulting precipitate is collected by vacuum filtration and dried under vacuum. The crude product is purified by known method.

Other methods known to those of skill in the art can be similarly used for the preparation of alkyl ester compounds provided herein.

D. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with viral infections, inappropriate cell proliferation or bone metabolism and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with associated with viral infections, inappropriate cell proliferation or bone metabolism. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with viral infections, inappropriate cell proliferation or bone metabolism, as described herein.

In one embodiment, a therapeutically effective dosage should produce a serum concentration of active ingredient of from about 0.1 ng/ml to about 50-100 μg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%–100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of diseases or disorders associated with viral infections, inappropriate cell proliferation or bone metabolism, within the packaging material, and a label that indicates that the compound or composition, or pharmaceutically acceptable derivative thereof, is used for the treatment, prevention or amelioration of one or more symptoms of diseases or disorders associated with viral infections, inappropriate cell proliferation or bone metabolism.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder associated with viral infections, inappropriate cell proliferation or bone metabolism.

E. Evaluation of the Activity of the Compounds

The activity of the compounds as antivirals can be measured in standard assays known in the art. Exemplary assays are described herein.

Determination of Antiviral Activity and Drug Cytotoxicity (VV and CV Activity)

The tables below show $CC_{50}$ and $EC_{50}$ data for exemplary compounds. In Table 1, antiviral activity and cytotoxicity of compounds provided herein against vaccinia virus (VV) and cowpox virus (CV) in human foreskin fibroblast (HFF) cells infected with VV or CV in plaque reduction assay and neutral red uptake assay known in the art was measured. Eicosyl-(S)-HPMPA and 15-methyl-hexadecyloxyethyl-(S)-HPMPA show $EC_{50}$ less than 0.5 μM in this assay.

HCMV and MCMV Activity i) Cell Cultures and Viruses

Human foreskin fibroblast (HFF) cells and mouse embryo fibroblast (MEF) cells are prepared as primary cultures and used in the HCMV and MCMV assays. Cells are propagated in minimal essential medium (MEM) containing 10% fetal bovine serum (FBS), 2 mM L-glutamine, 100 U of penicillin per ml and 25 μg of gentamicin per ml in T-175 cm2 tissue culture flasks (BD Falcon, Bedford, Mass.) until used in antiviral assays. HCMV strain AD-169 and MCMV strain Smith are propagated by using standard virological techniques.

(ii) Neutral Red Uptake Assay for Cytotoxicity.

HFF cells are seeded into 96-well tissue culture plates at 2.5×104 cells/well. After a 24-h incubation, medium is replaced with MEM containing 2% FBS, and an alkyl ester provided herein is added to the first row and then diluted serially fivefold from 100 to 0.03 μM. The plates are incubated for 7 days, and cells are stained with neutral red and incubated for 1 h. Plates are shaken on a plate shaker for 15 min, and neutral red is solubilized with 1% glacial acetic acid-50% ethanol. The optical density is read at 540 nm. The concentration of drug that reduced cell viability by 50% ($CC_{50}$) is calculated by using computer software. MEF cells are stained with neutral red and evaluated visually with a stereomicroscope at ×10 magnification. No toxicity was observed in the MCMV assays at the concentrations tested.

The $CC_{50}$ data for exemplary compounds is shown in Tables 1 and 2.

(iii) Plaque Reduction Assay for Antiviral Activity.

HFF or MEF cells are placed into 6- or 12-well plates and incubated at 37° C. for 2 days (HFF) or 1 day (MEF). Ganciclovir and CDV are used as positive controls. Virus is diluted in MEM containing 10% FBS to provide 20 to 30 plaques per well. The medium is aspirated, and 0.2 ml of virus is added to each well in triplicate with 0.2 ml of medium added to drug toxicity wells. The plates are incubated for 1 h with shaking every 15 min. An alkyl ester provided herein is serially diluted 1:5 in MEM with 2% FBS starting at 100 μM and added to appropriate wells. Following a 7-day incubation for MCMV, or 8 days for HCMV, cells are strained for 6 h with 2 ml of 5.0% neutral red in phosphate-buffered saline. The stain is aspirated, and plaques were counted by using a

TABLE 1

Efficacy and Cytotoxicity of alkyl esters of Cidofovir (CDV) and cyclic Cidofovir (cCDV) in Vaccinia Copenhagen and Cowpox Brighton

| Compound | Abbreviation | $CC_{50}$ (μM)[a] | Vaccinia Copenhagen | | Cowpox Brighton | |
| --- | --- | --- | --- | --- | --- | --- |
| | | | $EC_{50}$ (μM)[a] | SI[b] | $EC_{50}$ (μM)[a] | SI[b] |
| Cidofovir Series | | | | | | |
| Cidofovir | CDV | >317 ± 0 | 31 ± 5.4 | >10 | 42 ± 5.4 | >7.5 |
| R group | | | | | | |
| Octyl- (8) | O-CDV | >100 | >20 ± 0 | — | >20 ± 0 | — |
| Dodecyl- (12) | DD-CDV | >100 | >20 ± 0 | — | >20 ± 0 | — |
| Hexadecyl- (16) | HD-CDV | >157 ± 58 | 3.1 ± 0.1 | >51 | 6.0 ± 2.0 | >26 |
| Eicosyl- (20) | EC-CDV | 45 ± 8.5 | 1.6 ± 1.3 | 28 | 1.5 ± 0.9 | 30 |
| Tetracosyl- (24) | TC-CDV | >100 | >17 ± 4.2 | — | >20 ± 0 | — |

[a]Values are the means of two or more assays (± standard deviation)
[b]SI = $CC_{50}/EC_{50}$
[c]Values in parentheses are the numbers of atoms beyond the phosphate oxygen.

stereomicroscope at ×10 magnification. By comparing drug-treated with untreated wells, 50% effective concentrations ($EC_{50}$s) are calculated in a standard manner. The $EC_{50}$ data for exemplary compounds is shown in Table 2.

TABLE 2

Efficacy and Cytotoxicity of alkyl esters of Cidofovir (CDV) and cyclic Cidofovir (cCDV) for HCMV and MCMV

| Compound | Abbreviation | $CC_{50}$ (µM)$^a$ | HCMV $EC_{50}$ (µM)$^a$ | SI | MCMV $EC_{50}$ (µM)$^a$ | SI |
|---|---|---|---|---|---|---|
| Cidofovir Series | | | | | | |
| Cidofovir R group | CDV | >317 ± 0 | 1.2 ± 0.43 | 264 | 0.04 ± 0.03 | >7925 |
| Octyl- (8:0) | O-CDV | >100 | 5.25 ± 5.7 | >19 | >10 | <10 |
| Dodecyl-(12:0) | DD-CDV | >100 | 0.31 ± 0.19 | >322 | >10 | <10 |
| Hexadecyl- (16:0) | HD-CDV | >157 ± 58 | 0.005 ± 0 | >31400 | 0.02 ± 0 | >7850 |
| Eicosyl- (20:0) | EC-CDV | 38.5 | 0.0007 | 5500 | 0.005 ± 0 | 7700 |
| Docosyl- (22:0) | DC-CDV | 79.6 | 0.004 | >26500 | 0.85 ± 0.007 | 995 |
| Tetracosyl- (24:0) | TC-CDV | >100 | 0.006 ± 0.03 | 1670 | 7.45 ± 0.64 | >13 |
| Cyclic Cidofovir Series | | | | | | |
| Cyclic Cidofovir R group | cCDV | >331 ± 0 | 3.1 ± 1.8 | >107 | 0.23 ± 0.07 | >1439 |
| Octyl- (8:0) | O-cCDV | Nd | Nd | Nd | Nd | Nd |
| Dodecyl-(12:0) | DD-cCDV | Nd | Nd | Nd | Nd | Nd |
| Hexadecyl- (16:0) | HD-cCDV | 83 ± 20 | 3.10 ± 2.35 | 26.8 | 0.13 ± 0.01 | 6638 |
| Eicosyl- (20:0) | EC-cCDV | 86.1 | 0.011 | 7827 | 0.23 ± 0.01 | 374 |
| Docosyl- (22:0) | DC-cCDV | >100 | 0.032 | >3125 | 2.8 ± 1.7 | >36 |
| Tetracosyl- (24:0) | TC-cCDV | >100 | 0.32 | >313 | 2.3 ± 1.3 | >43 |

Nd = not determined
$^a$Values are the means of two or more assays (±standard deviation)
$^b$SI = $CC_{50}/EC_{50}$
Values in parentheses are the numbers of atoms beyond the phosphate oxygen; the number after the colon is the number of double bonds in the alkyl chain.
Data are recorded as the means ± standard deviations of at least two determinations. Values without a standard deviation represent a single determination. SI, selective index ($CC_{50}/EC_{50}$).

F. Methods of Use of the Compounds and Compositions

Methods of treating, preventing, or ameliorating one or more symptoms of diseases associated with viral infections, inappropriate cell proliferation and bone metabolism using the compounds and compositions provided herein are provided. In practicing the methods, effective amounts of the compounds or compositions containing therapeutically effective concentrations of the compounds are administered. In certain embodiments, the methods provided herein are for the preventing, or ameliorating one or more symptoms of diseases associated with viral infections, including, but not limited to influenza; hepatitis B and C virus; cytomegalovirus (CMV); herpes infections, such as those caused by Varicella zoster virus, Herpes simplex virus types 1 & 2, Epstein-Barr virus, Herpes type 6 (HHV-6) and type 8 (HHV-8); Varicella zoster virus infections such as shingles or chicken pox; Epstein Barr virus infections, including, but not limited to infectious mononucleosis/glandular; retroviral infections including, but not limited to SIV, HIV-1 and HIV-2; ebola virus; adenovirus and papilloma virus.

In further embodiments, the methods provided herein are for the preventing, treating, or ameliorating one or more symptoms of diseases associated with viral infections caused by orthopox viruses, such as variola major and minor, vaccinia, smallpox, cowpox, camelpox, and monkeypox.

In one embodiment, a therapeutically effective dosage to treat such an orthopox infection should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared, e.g., to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In certain embodiments, the methods provided herein are for the preventing, or ameliorating one or more symptoms of diseases associated with cell proliferation, including, but not limited to cancers. Examples of cancers include, but are not limited to, lung cancer, head and neck squamous cancers, colorectal cancer, prostate cancer, breast cancer, acute lymphocytic leukemia, adult acute myeloid leukemia, adult non Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, and skin cancer.

Methods of treating, preventing, or ameliorating one or more symptoms associated with bone metabolism by administering a compound or composition provided herein are provided. Such diseases include, but are not limited to osteoporosis, such as senile, post-menopausal or steroid-induced osteoporosis, metastatic bone cancers, Paget's disease, osteogenesis imperfecta, fibrous dysplasia, rheumatoid arthritis, hyperparathyroidism, algodystrophy, sterno-costoclavicular hyperostosis, Gaucher's disease, Engleman's disease, certain non-skeletal disorders and periodontal disease. An example of an effective amount is an amount that will prevent, attenuate, or reverse abnormal or excessive bone resorption or the bone resorption that occurs in the aged, particularly postmenopausal females or prevent or oppose bone metastasis and visceral metastasis in breast cancer.

Combination Therapy

The compounds and compositions provided herein may also be used in combination with other active ingredients. In certain embodiments, the compounds may be administered in combination, or sequentially, with another therapeutic agent. Such other therapeutic agents include those known for treatment, prevention, or amelioration of one or more symptoms associated with viral infections, inappropriate cell proliferation and bone metabolism. Such therapeutic agents include, but are not limited to, antiviral agents, anti-neoplastic agents and agents for the treatment and/or prevention of symptoms associated bone metabolism. In certain embodiments, the compounds provided herein may be administered in combination with one or more antiviral agents or anti-cancer agents. Anti-cancer agents for use in combination with the instant compounds include, but are not limited to, alkylating agents, toxins, antiproliferative agents and tubulin binding agents. Classes of cytotoxic agents for use herein include, for example, the anthracycline family of drugs, the vinca drugs, the mitomycins, the bleomycins, the cytotoxic nucleosides, the pteridine family of drugs, diynenes, the maytansinoids, the epothilones, the taxanes and the podophyllotoxins.

It should be understood that any suitable combination of the compounds provided herein with one or more of the above-mentioned compounds and optionally one or more further pharmacologically active substances are considered to be within the scope of the present disclosure. In another embodiment, the compound provided herein is administered prior to or subsequent to the one or more additional active ingredients.

The following examples are provided for illustrative purposes only and are not intended to limit the scope of the invention.

EXAMPLES 1H and 31P nuclear magnetic resonance (NMR) spectra were recorded on a Varian HG-400 spectrometer with tetramethylsilane (internal) and 85% D3PO4 in D2O (external) as references for 1H and 31P (0.00 ppm), respectively. Electrospray ionization mass spectroscopy (ESI) was performed by HT Laboratories (San Diego, Calif.). Chromatographic purification was done by the flash method with Merck silica gel 60 (240 to 400 mesh). All final products were homogeneous by thin-layer chromatography performed on Analtech 250-μm Silica Gel GF Uniplates visualized under UV light, with phospray (Supelco, Bellafonte, Pa.), and by charring (400° C.). Cyclic cidofovir dihydrate was prepared by the method of Louie and Chapman (Nucleosides & Nucleic Acids, 20:1099-1102; 2001). Bromoalkanes and bromoalkoxyalkanes were either commercially available or synthesized from the corresponding alcohol. All other chemicals were of reagent quality and used as obtained from the suppliers. All reactions were carried out in an inert atmosphere (dry nitrogen).

Example 1

Octyl Cyclic Cidofovir 1-bromooctane (1.2 eq) was added to a suspension of cyclic cidofovir (cCDV) dihydrate, N,N-dicyclohexyl-4-morpholino-carboxamidine (1.1 eq) and N,N-dimethylformamide (10 ml/mmol). The mixture was heated to 60° C. and stirred magnetically overnight. The solvent was then evaporated under reduced pressure, the residue was adsorbed onto silica gel and purified by flash column chromatography (elution gradient, $CH_2Cl_2$ to 15% EtOH). The Octyl cyclic cidofovir was isolated as equimolar mixtures of the axial and equatorial diastereomers.

Yield 46%; $^1$H NMR ($CDCl_3$+$CD_3OD$) δ 7.00 (dd, J=7.4 Hz, J=10 Hz, 1H), 5.44 (d, J=7.4 Hz, 1H), 3.99 to 4.29 (m, 2H), 3.64 to 3.86 (m, 6H), 3.50 to 3.58 (m, 2H), 3.12 to 3.33 (m, 1H), 1.28 to 1.39 (m, 2H), 0.75 to 1.15 (m, 10H), 0.52 (t, J=6.8 Hz); $^{31}$P NMR δ 12.31, 13.58.

MS (ESI): m/z 374 (M+H)$^+$, 372 (M–H)$^-$.

Example 2

Dodecyl Cyclic Cidofovir

The title compound was prepared using the same procedure as described for Example 1 using 1-bromododecane and cyclic cidofovir.

Yield 45%; $^1$H NMR ($CDCl_3$+$CD_3OD$) δ 7.02 (dd, J=7.1 Hz, J=10 Hz, 1H), 5.47 (d, J=7.4 Hz, 1H), 4.03 to 4.07 (m, 2H), 3.69 to 3.89 (m, 6H), 3.53 to 3.60 (m, 2H), 3.15 to 3.35 (m, 1H), 1.32 to 1.42 (m, 2H), 0.86 to 1.15 (m, 10H), 0.54 (t, J=6.0 Hz); $^{31}$P NMR ($CDCl_3$+$CD_3OD$) δ=12.22, 13.51. MS (ESI): m/z 430 (M+H)$^+$, 452 (M+Na)$^+$; 428 (M–H)$^-$.

Example 3

Hexadecyl Cyclic Cidofovir

The title compound was prepared using the same procedure as described for Example 1 using 1-bromohexadecane and cyclic cidofovir.

Yield 55%; $^1$H NMR (di-methyl sulfoxide [DMSO]-$d_6$) δ 7.48 (dd, J=31.2, 7.2 Hz, 1H), 7.108 (br d, J=39.9 Hz, 2H), 5.64 (t, J=6.8 Hz, 1H), 3.5 to 4.9 (m, 711), 1.60 (br s, 2H), 1.24 (br s, 28H), 0.86 (t, J=6.5 Hz, 3H); $^{31}$P NMR ($CDCl_3$+$CD_3OD$) δ=12.18, 13.58. MS (ESI): m/z 486 (MH)$^+$, 484 (M–H)$^-$.

Example 4

Eicosyl Cyclic Cidofovir (EC-cCDV)

The title compound was prepared using the same procedure as described for Example 1 using 1-bromoeicosane and cyclic cidofovir.

Yield 8%; $^1$H NMR (DMSO-$d_6$) δ 7.43 (d, J=7.2 Hz, 1H), 7.08 (br d, J=30.9 Hz 2H), 5.61 (d, J=6.9 Hz, 1H), 3.5 to 4.9 (m, 7H), 1.60 (br s, 2H), 1.24 (br s, 36H), 0.86 (t, J=6.5 Hz, 3H); $^{31}$P NMR δ=14.02, 12.81; MS (ESI): m/z 564 (M+Na)$^+$, 542 (M+H)$^+$.

Example 5

Tetracosyl Cyclic Cidofovir

The title compound was prepared using the same procedure as described for Example 1 using 1-bromotetracosane and cyclic cidofovir.

Yield 17%; $^1$H NMR (DMSO-$d_6$) δ 7.43 (d, J=6.9 Hz, 1H), 7.07 (br d, J=25.5 Hz 2H), 5.63 (d, J=6.9 Hz, 1H), 3.1 to 4.0 (m, 7H), 1.60 (br s, 2H), 1.22 (br s, 44H), 0.84 (t, J=6.5 Hz, 3H); $^{31}$P NMR (CDCl$_3$+CD$_3$OD) δ 12.66, 13.86. MS (ESI): m/z 620 (M+Na)$^+$, 598 (M+H)$^+$.

Example 6

Docosyl Cyclic Cidofovir

The title compound was prepared by Mitsunobu reaction. Anhydrous cCDV (1 eq), the docosanol (2 eq), and tri-phenylphosphine (2 eq) were dissolved or suspended in anhydrous N,N-dimethylformamide (6.5 ml per mmol of cCDV) and stirred vigorously under a nitrogen atmosphere. Diisopropyl azadicarboxylate (2 eq) was then added in three portions over 15 min before the mixture was allowed to stir overnight. The solvent was then evaporated under vacuum, and the residue was adsorbed onto silica gel and purified by column chromatography. Gradient elution from 100% CH2Cl2 to 15% EtOH was followed by recrystallization from p-dioxane. The coupled product was isolated as equimolar mixtures of axial and equatorial diastereomers.

Yield 26%; $^1$H NMR (DMSOd$_6$) δ 7.43 (d, J=7.2 Hz, 1H), 7.07 (br d, J=25.5 Hz 2H), 5.61 (d, J=6.9 Hz, 1H), 3.3 to 4.4 (m, 7H), 1.60 (br s, 2H), 1.23 (br s, 40H), 0.86 (t, J=6.5 Hz, 3H); $^{31}$P NMR δ 12.80; MS (ESI): m/z 564 (M+Na)$^+$, 570 (M+H)$^+$, 604 (MCl)$^-$, 568 (–H)$^-$.

Example 7

1-O-Octadecyl-2-O-benzyl-sn-glycero-3-cCDV (ODBGcCDV)

Yield 45%; $^1$H NMR (CDCl$_3$) δ 7.27 to 7.38 (m, 7H), 7.16 and 7.30 (pair of doublets, 1H), 5.72 and 5.68 (pair of doublets, 1H), 4.68 and 4.62 (pair of singlets, 2H), 3.97 to 4.40 (m, 9H), 3.44 (t, 2H), 3.41 (t, 2H), 3.25 (m, 1H), 1.54 (m, 2H), 1.26 (br s, 30H), 0.88 (t, 3H); $^{31}$P NMR δ13.72 and 12.01; MS (ESI) m/z 678 (M+H)$^+$, 700 (M+Na)$^+$, 676 (M–H)$^-$.

Example 8

Octyl Cidofovir, Sodium Salt

The octyl cyclic CDV analog was suspended in 2 M NaOH (25 ml/mmol). The suspensions was heated to 80° C. and stirred for 1 h, during which the mixtures became clear. After hydrolysis, the solution was cooled to 25° C. and acidified with glacial acetic acid (pH approximately 5). The resulting precipitate was collected by vacuum filtration and dried under vacuum. The crude product was purified either by flash column chromatography (eluant, CH2Cl2-20% MeOH) and recrystallized to purity from ethanol (2).

Yield 46%; $^1$H NMR (DMSO-d$_6$) δ 7.53 (d, J=7.5 Hz, 1H), 7.12 (br d, J=58.5 Hz 2H), 5.64 (d, J=7.5 Hz, 1H), 3.20 to 3.80 (m, 7H), 1.42 (br s, 2H), 1.24 (br s, 12H), 0.85 (t, J=6.5 Hz, 3H); $^{31}$P NMR δ 14.46; MS (ESI): m/z 436 (M+2Na)$^+$, 414 (M+Na)$^+$; 390 (M–H)$^-$.

The following acyclic analogs were prepared using similar procedure.

Example 9

Dodecyl Cidofovir, Sodium Salt

Yield 32%; $^1$H NMR (DMSO-d$_6$) δ 7.54 (d, J=7.2 Hz, 1H), 7.19 (br d, J=57.3 Hz 2H), 5.67 (d, J=7.2 Hz, 1H), 3.20 to 3.81 (m, 7H), 1.42 (br s, 2H), 1.22 (br s, 20H), 0.84 (t, J=6.5 Hz, 3H); $^{31}$P NMR δ 14.60; MS (ESI): m/z 492 (M+2Na)$^+$, 470 (M+Na)$^+$; 446 (M–H)$^-$.

Example 10

Hexadecyl Cidofovir, Sodium Salt

Yield 43%; $^1$H NMR (DMSO-d$_6$) δ 7.52 (d, J=7.2 Hz, 1H), 7.19 (br d, J=57.3 Hz, 2H), 5.65 (d, J=7.2 Hz, 1H), 3.2 to 3.9 (m, 7H), 1.45 (br s, 2H), 1.24 (br s, 28H), 0.86 (t, J=6.5 Hz, 3H); $^{31}$P NMR (D$_2$O) δ=16.73; MS (ESI): m/z 504 (M+Na)$^+$, 526 (M+2Na)$^+$, 502 (M–H)$^-$.

Example 11

Eicosyl Cidofovir, Sodium Salt (EC-CDV)

Yield 39%; $^1$H NMR (DMSO-d$^8$) δ=7.49 (d, J=7.2 Hz, 1H), 7.01 (br d, J=45.3 Hz 2H), 5.60 (d, J=7.2 Hz, 1H), 3.2 to 3.9 (m, 7H), 1.42 (br s, 2H), 1.26 (br s, 36H), 0.85 (t, J=6.5 Hz, 3H); $^{31}$P NMR δ=14.22; MS (ESI): m/z 604 (M+2Na)$^+$, 582 (M+Na)$^+$; 558 (M–H)$^-$.

Example 12

Docosyl Cidofovir, Sodium Salt

Yield 57%; $^1$H NMR (DMSO-d$_6$) δ 7.50 (d, J=7.2 Hz, 1H), 7.03 (br d, J=50.4 Hz 2H), 5.60 (d, J=7.2 Hz, 1H), 3.2 to 3.9 (m, 7H), 1.42 (br s, 2H), 1.22 (br s, 40H), 0.85 (t, J=6.5 Hz, 3H); $^{31}$P NMR δ14.21; MS (ESI): m/z 632 (M+2Na)$^+$, 582 (M–H, sodium salt plus H)$^+$; 540 (M–H)$^-$, 576 (M–Cl).

Example 13

Tetracosyl Cidofovir, Sodium Salt

Yield 35%; $^1$H NMR (CDCl$_3$+methanol d$^4$) δ 7.19 (d, J=7.4 Hz, 1H), 5.41 (d, J=7.4 Hz, 1H), 3.03 to 3.62 (m, 7H), 2.90 to 2.91 (m, 2H), 1.10 to 1.22 (m, 2H), 0.83 (br s, 42H), 0.45 (t, J=6.9 Hz). $^{31}$P NMR (CDCl$_3$+methanol d$^4$) δ=16.14. MS (ESI): m/z 638 (M+H, sodium salt plus H)$^+$, 660 (M+Na, sodium salt of sodium salt)$^+$; 614 (free acid)$^-$.

Since modifications will be apparent to those of skill in the art, it is intended that the invention be limited only by the scope of the appended claims.

What is claimed is:

1. A compound having the following formula:

or a pharmaceutically acceptable derivative thereof,
wherein P$^x$ is a cyclic cidofovir, O is an oxygen atom, and R is selected from the group consisting of eicosyl, docosyl and tetracosyl.

2. The compound of claim 1, wherein R is eicosyl or docosyl.

3. The compound of claim 1, wherein the compound is eicosyl cyclic cidofovir.

4. The compound of claim 1, wherein the compound is docosyl cyclic cidofovir.

5. A pharmaceutical composition comprising the compound of claim 1 and a pharmaceutically acceptable carrier.

6. An article of manufacture, comprising packaging material and the compound of claim 1, contained within the packaging material, wherein the compound is effective for treatment of a disease associated with a viral infection and the packaging material includes a label that indicates that the compound is used for treatment of a disease associated with the viral infection, wherein said viral infection is influenza, hepatitis B virus, hepatitis C virus, cytomegalovirus, Varicella zoster virus, Herpes simplex virus type 1, Herpes simplex virus type 2, Herpes virus type 6, Herpes virus type 8, Epstein Barr virus, retrovirus, orthopox virus, ebola virus, adenovirus or papilloma virus.

7. A method for treating a viral infection in a mammal, wherein the method comprises administering to a subject in need thereof an effective amount of the compound of claim 1, wherein the viral infection is caused by influenza, hepatitis B virus, hepatitis C virus, cytomegalovirus, Varicella zoster virus, Herpes simplex virus type 1, Herpes, simplex virus type 2, Herpes virus type 6, Herpes virus type 8, Epstein Barr virus, retrovirus, orthopox virus, ebola virus, adenovirus or papilloma virus.

8. The method according to claim 7, wherein the viral infection is an orthopox viral infection selected from the group consisting of smallpox, cowpox, camelpox, and monkeypox.

9. The method according to claim 7, wherein the viral infection is a herpes viral infection.

10. The method according to claim 7, wherein the viral infection is a hepatitis B or a hepatitis C infection.

* * * * *